(12) United States Patent
Plakogiannis et al.

(10) Patent No.: US 12,186,280 B2
(45) Date of Patent: *Jan. 7, 2025

(54) PHARMACEUTICAL COMPOSITION AND METHOD FOR TREATING SEIZURE DISORDERS

(71) Applicant: Pike Therapeutics Inc., Vancouver (CA)

(72) Inventors: Fotios M. Plakogiannis, Whitestone, NY (US); Tamanna Lather, Jersey City, NJ (US); Nisarg Modi, Jersey City, NJ (US); Marina Borovinskaya, East Brunswick, NJ (US)

(73) Assignee: Pike Therapeutics Inc., Vancouver (CA)

( * ) Notice: Subject to any disclaimer, the term of this patent is extended or adjusted under 35 U.S.C. 154(b) by 238 days.

This patent is subject to a terminal disclaimer.

(21) Appl. No.: 17/065,851

(22) Filed: Oct. 8, 2020

(65) Prior Publication Data

US 2021/0113489 A1 Apr. 22, 2021

Related U.S. Application Data

(60) Provisional application No. 62/913,874, filed on Oct. 11, 2019.

(51) Int. Cl.
*A61K 31/05* (2006.01)
*A61K 9/70* (2006.01)

(52) U.S. Cl.
CPC ............ *A61K 31/05* (2013.01); *A61K 9/7023* (2013.01)

(58) Field of Classification Search
CPC .............................. A61K 31/05; A61K 9/7023
See application file for complete search history.

(56) References Cited

U.S. PATENT DOCUMENTS

| | | | |
|---|---|---|---|
| 6,113,940 A | 9/2000 | Brooke et al. | |
| 6,194,000 B1 | 2/2001 | Smith | |
| 6,245,347 B1 | 6/2001 | Zhang et al. | |
| 6,280,770 B1 | 8/2001 | Pather et al. | |
| 6,328,992 B1 | 12/2001 | Brooke et al. | |
| 6,689,379 B1 | 2/2004 | Bracht | |
| 6,692,771 B2 | 2/2004 | Pather et al. | |
| 6,855,735 B2 | 2/2005 | Friedman | |
| 6,946,150 B2 | 9/2005 | Whittle | |
| 7,025,992 B2 | 4/2006 | Whittle et al. | |
| 7,544,676 B2 | 6/2009 | Dolle et al. | |
| 7,592,328 B2 | 9/2009 | Jarho et al. | |
| 7,622,140 B2 | 11/2009 | Whittle et al. | |
| 7,671,052 B2 | 3/2010 | Dolle et al. | |
| 7,709,536 B2 | 5/2010 | Whittle | |
| 7,776,314 B2 | 8/2010 | Bartholomaus et al. | |
| 7,807,711 B2 | 10/2010 | Korthout et al. | |
| 7,968,594 B2 | 6/2011 | Guy et al. | |
| 8,071,641 B2 | 12/2011 | Weiss et al. | |
| 8,114,383 B2 | 2/2012 | Bartholomaus et al. | |
| 8,137,711 B2 | 3/2012 | Wolicki | |
| 8,211,946 B2 | 7/2012 | Whittle | |
| 8,246,981 B2 | 8/2012 | Patel et al. | |
| 8,293,786 B2 | 10/2012 | Stinchcomb et al. | |
| 8,309,060 B2 | 11/2012 | Bartholomaus et al. | |
| 8,435,556 B2 | 5/2013 | Stinchcomb et al. | |
| 8,449,908 B2 | 5/2013 | Stinchcomb et al. | |
| 8,481,085 B2 | 7/2013 | Musty et al. | |
| 8,603,515 B2 | 12/2013 | Whittle | |
| 8,642,645 B2 | 2/2014 | Kelly | |
| 8,771,760 B2 | 7/2014 | Guy et al. | |
| 8,992,908 B2 | 3/2015 | Smith et al. | |
| 9,029,423 B2 | 5/2015 | Whittle | |
| 9,034,395 B2 | 5/2015 | Whittle et al. | |
| 9,205,063 B2 | 12/2015 | Guy et al. | |
| 9,272,037 B2 | 3/2016 | Singh | |
| 9,304,134 B2 | 4/2016 | Smith | |
| 9,375,417 B2 | 6/2016 | Smith et al. | |
| 9,533,942 B2 | 1/2017 | Stinchcomb et al. | |
| 9,533,982 B2 | 1/2017 | Conn et al. | |
| 9,603,887 B2 | 3/2017 | Kelly | |
| 9,763,912 B2 | 9/2017 | Chen et al. | |
| 9,833,433 B1 | 12/2017 | Chen et al. | |
| 9,918,961 B2 | 3/2018 | Hearn et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 9,957,321 B2 | 5/2018 | Smith et al. | |

(Continued)

FOREIGN PATENT DOCUMENTS

| | | |
|---|---|---|
| CA | 2859930 A1 | 3/2016 |
| CA | 2938621 C | 5/2019 |
| CA | 3175771 A1 | 10/2021 |
| CA | 3213953 A1 | 10/2022 |
| CN | 108785298 | 11/2018 |
| JP | 2001131089 A | 5/2001 |
| JP | 2012525416 | 10/2012 |
| JP | 20155512418 A | 4/2015 |
| WO | 2001003668 | 1/2001 |
| WO | 2001064149 | 9/2001 |
| WO | 2002064109 | 8/2002 |
| WO | 2002069993 | 9/2002 |
| WO | 2002089945 | 11/2002 |
| WO | 2003105800 | 12/2003 |

(Continued)

OTHER PUBLICATIONS

Valenta, Claudia et al., "The use of polymers for dermal and transdermal delivery", European Journal of Pharmaceutics and Biopharmaceutics, pp. 279-289, vol. 58(2).

(Continued)

*Primary Examiner* — Trevor Love
(74) *Attorney, Agent, or Firm* — Joseph F. Murphy; Potomac Law Group, PLLC

(57) ABSTRACT

The present disclosure relates to the transdermal administration of cannabidiol (CBD) for the reduction of seizure frequency in the treatment of "treatment-resistant epilepsy" (TRE).

16 Claims, No Drawings

(56) References Cited

U.S. PATENT DOCUMENTS

| | | |
|---|---|---|
| 9,962,340 B2 | 5/2018 | Weimann |
| 9,962,341 B2 | 5/2018 | Stott et al. |
| 10,004,684 B2 | 6/2018 | Whittle et al. |
| 10,028,904 B2 | 7/2018 | Smith et al. |
| 10,092,525 B2 | 10/2018 | Guy et al. |
| 10,098,867 B2 | 10/2018 | Javid et al. |
| 10,098,895 B2 | 10/2018 | Chang et al. |
| 10,111,840 B2 | 10/2018 | Guy et al. |
| 10,118,006 B2 | 11/2018 | Davidson et al. |
| 10,137,095 B2 | 11/2018 | Guy et al. |
| 10,155,018 B1 | 12/2018 | Jenn |
| 10,172,809 B2 | 1/2019 | Aung-Din |
| 10,195,159 B2 | 2/2019 | Whittle et al. |
| 10,213,390 B1 | 2/2019 | Bonn-Miller et al. |
| 10,272,125 B2 | 4/2019 | Weimann |
| 10,278,996 B2 | 5/2019 | Avidov et al. |
| 10,307,392 B2 | 6/2019 | Kariman |
| 10,314,792 B2 | 6/2019 | Sebree et al. |
| 10,383,816 B2 | 8/2019 | Aung-Din |
| 10,413,521 B2 | 9/2019 | Hearn et al. |
| 10,420,809 B2 | 9/2019 | Crowley |
| 10,471,022 B2 | 11/2019 | Bonn-Miller et al. |
| 10,538,373 B2 | 1/2020 | Whittle |
| 10,555,927 B2 | 2/2020 | Jenn |
| 10,568,848 B2 | 2/2020 | Sebree et al. |
| RE47,885 E | 3/2020 | Strinchcomb et al. |
| 10,588,869 B2 | 3/2020 | Weimann |
| 10,588,871 B1 | 3/2020 | Fracassi et al. |
| 10,588,974 B2 | 3/2020 | Leone-Bay et al. |
| 10,603,288 B2 | 3/2020 | Guy et al. |
| 10,617,733 B2 | 4/2020 | Kelly |
| 10,632,064 B2 | 4/2020 | Aung-Din |
| 10,660,872 B2 | 5/2020 | Sarne |
| 10,675,240 B2 | 6/2020 | Smith et al. |
| 10,675,264 B2 | 6/2020 | Green et al. |
| 10,695,287 B2 | 6/2020 | Robbins et al. |
| 10,709,671 B2 | 7/2020 | Guy et al. |
| 10,709,673 B2 | 7/2020 | Guy |
| 10,709,674 B2 | 7/2020 | Guy et al. |
| 10,709,748 B2 | 7/2020 | Witowski et al. |
| 10,716,766 B2 | 7/2020 | Aung-Din |
| 10,751,299 B2 | 8/2020 | Ghalili |
| 10,758,497 B2 | 9/2020 | Bonn-Miller et al. |
| 10,758,514 B2 | 9/2020 | Liu et al. |
| 10,799,545 B2 | 10/2020 | Weimann |
| 10,807,777 B2 | 10/2020 | Whittle |
| 10,828,266 B2 | 11/2020 | Aung-Din |
| 10,849,860 B2 | 12/2020 | Guy et al. |
| 10,864,189 B2 | 12/2020 | Borok |
| 10,869,842 B1 | 12/2020 | Summers |
| 10,881,606 B2 | 1/2021 | Schmitz et al. |
| 10,918,608 B2 | 2/2021 | Guy et al. |
| 10,918,686 B2 | 2/2021 | Siurkus |
| 10,945,967 B2 | 3/2021 | Song |
| 10,966,939 B2 | 4/2021 | Guy et al. |
| 11,026,896 B2 | 6/2021 | Fitzsimmons et al. |
| 11,052,055 B2 | 7/2021 | Kochinke |
| 11,065,209 B2 | 7/2021 | Guy et al. |
| 11,065,227 B2 | 7/2021 | Stott et al. |
| 11,096,905 B2 | 8/2021 | Guy et al. |
| 11,116,730 B2 | 9/2021 | Fracassi et al. |
| 11,147,799 B2 | 10/2021 | Kopsky et al. |
| 11,154,516 B2 | 10/2021 | Guy et al. |
| 11,154,517 B2 | 10/2021 | Guy et al. |
| 11,160,795 B2 | 11/2021 | Guy et al. |
| 11,207,292 B2 | 12/2021 | Guy et al. |
| 2002/0019421 A1 | 2/2002 | Biberman |
| 2004/0033254 A1* | 2/2004 | Song ............... A61K 31/196 424/449 |
| 2004/0138293 A1 | 7/2004 | Werner et al. |
| 2005/0038062 A1 | 2/2005 | Burns et al. |
| 2005/0042271 A1 | 2/2005 | Xiong et al. |
| 2005/0070596 A1 | 3/2005 | Baker et al. |
| 2006/0039959 A1 | 2/2006 | Wessling |
| 2006/0135599 A1 | 6/2006 | Symonds |
| 2007/0060638 A1 | 3/2007 | Olmstead et al. |
| 2007/0072939 A1 | 3/2007 | Kupper |
| 2007/0083186 A1 | 4/2007 | Carter et al. |
| 2008/0112895 A1 | 5/2008 | Kottayil |
| 2009/0197941 A1 | 8/2009 | Guy et al. |
| 2009/0298929 A1 | 12/2009 | Jarho |
| 2010/0035978 A1 | 2/2010 | Guy et al. |
| 2010/0168108 A1 | 7/2010 | Dolle et al. |
| 2010/0184848 A1 | 7/2010 | Wine et al. |
| 2010/0273895 A1 | 10/2010 | Stinchcomb et al. |
| 2010/0286098 A1 | 11/2010 | Robson et al. |
| 2010/0317729 A1 | 12/2010 | Guy et al. |
| 2011/0021617 A1 | 1/2011 | Korthout |
| 2011/0052694 A1 | 3/2011 | Stinchcomb et al. |
| 2012/0034293 A1 | 2/2012 | Stinchcomb et al. |
| 2012/0309823 A1 | 12/2012 | Suzuki et al. |
| 2013/0022687 A1 | 1/2013 | Fitzgerald, Jr. et al. |
| 2013/0122077 A1 | 5/2013 | Al-Ghananeem |
| 2013/0245110 A1 | 9/2013 | Guy et al. |
| 2013/0253449 A1 | 9/2013 | Yoshitake et al. |
| 2013/0281388 A1 | 10/2013 | Deaver et al. |
| 2014/0039043 A1 | 2/2014 | Musty et al. |
| 2014/0050787 A1 | 2/2014 | Tygesen et al. |
| 2014/0112984 A1 | 4/2014 | Arkenau-Maric et al. |
| 2014/0314757 A1 | 10/2014 | Sanchez et al. |
| 2015/0057306 A1 | 2/2015 | Fava et al. |
| 2015/0265720 A1 | 9/2015 | Levine et al. |
| 2015/0342902 A1 | 12/2015 | Vangara et al. |
| 2015/0342947 A1 | 12/2015 | Pollard et al. |
| 2015/0343071 A1 | 12/2015 | Vangara et al. |
| 2016/0000843 A1 | 1/2016 | Lowe et al. |
| 2016/0022627 A2 | 1/2016 | Smith |
| 2016/0039591 A1 | 2/2016 | Kinzer |
| 2016/0101069 A1 | 4/2016 | Charney et al. |
| 2016/0106808 A1 | 4/2016 | Charney et al. |
| 2016/0199304 A1 | 7/2016 | Nivorozhkin et al. |
| 2016/0220593 A1 | 8/2016 | Anastassov et al. |
| 2016/0256411 A1 | 9/2016 | Aung-Din |
| 2016/0271252 A1 | 9/2016 | Vangara et al. |
| 2016/0338974 A1 | 11/2016 | Aung-Din |
| 2016/0361271 A1 | 12/2016 | Weimann et al. |
| 2017/0020820 A1 | 1/2017 | Sackler |
| 2017/0035707 A1 | 2/2017 | Manthei et al. |
| 2017/0042791 A1 | 2/2017 | Ghalili et al. |
| 2017/0042878 A1 | 2/2017 | Fava et al. |
| 2017/0071870 A1 | 3/2017 | Weimann |
| 2017/0202895 A1 | 7/2017 | Hugh |
| 2017/0273914 A1 | 9/2017 | Knudsen |
| 2017/0306013 A1 | 10/2017 | Clark et al. |
| 2018/0021247 A1 | 1/2018 | Ghalili et al. |
| 2018/0042842 A1 | 2/2018 | Whittle et al. |
| 2018/0042845 A1 | 2/2018 | Sinai et al. |
| 2018/0049994 A1 | 2/2018 | Aung-Din |
| 2018/0071210 A1 | 3/2018 | Wilkhu et al. |
| 2018/0078512 A1 | 3/2018 | Weimann |
| 2018/0169035 A1 | 6/2018 | Eyal |
| 2018/0284402 A1 | 10/2018 | Hoag |
| 2018/0289665 A1 | 10/2018 | Turner et al. |
| 2018/0296498 A1 | 10/2018 | Kochinke |
| 2018/0311180 A1 | 11/2018 | Kochinke |
| 2018/0311181 A1 | 11/2018 | Kochinke |
| 2018/0311184 A1 | 11/2018 | Hoag |
| 2018/0318529 A1 | 11/2018 | Davidson et al. |
| 2018/0353463 A1 | 12/2018 | Winnicki |
| 2018/0360757 A1 | 12/2018 | Doroudian et al. |
| 2018/0369191 A1 | 12/2018 | Muscarella |
| 2019/0023780 A1 | 1/2019 | Smith et al. |
| 2019/0083388 A1 | 3/2019 | Gutterman et al. |
| 2019/0105298 A1 | 4/2019 | Eyal |
| 2019/0110981 A1 | 4/2019 | Weimann |
| 2019/0125779 A1 | 5/2019 | Ziburkus et al. |
| 2019/0133994 A1 | 5/2019 | Smith et al. |
| 2019/0134121 A1 | 5/2019 | Bermudez et al. |
| 2019/0167583 A1 | 6/2019 | Shah |
| 2019/0201372 A1 | 7/2019 | McKay |
| 2019/0224118 A1 | 7/2019 | Navon et al. |
| 2019/0224140 A1 | 7/2019 | Guy et al. |
| 2019/0231826 A1 | 8/2019 | Avidov et al. |
| 2019/0255014 A1 | 8/2019 | Gardner |

(56) References Cited

U.S. PATENT DOCUMENTS

| | | |
|---|---|---|
| 2019/0298683 A1 | 10/2019 | Friedman |
| 2019/0314297 A1 | 10/2019 | Gallily |
| 2019/0321355 A1 | 10/2019 | Anavi-Goffer |
| 2019/0321426 A1 | 10/2019 | Gallily |
| 2019/0328884 A1 | 10/2019 | Jones, Jr. et al. |
| 2019/0365667 A1 | 12/2019 | Wright et al. |
| 2020/0038421 A1 | 2/2020 | Anastassov et al. |
| 2020/0054887 A1 | 2/2020 | Levin |
| 2020/0078332 A1 | 3/2020 | Leone-Bay et al. |
| 2020/0085816 A1 | 3/2020 | Raz |
| 2020/0093755 A1 | 3/2020 | Biro et al. |
| 2020/0108027 A1 | 4/2020 | Whalley et al. |
| 2020/0129741 A1 | 4/2020 | Kawwas et al. |
| 2020/0138771 A1 | 5/2020 | Velasco Diez et al. |
| 2020/0138773 A1 | 5/2020 | Jenn |
| 2020/0163980 A1 | 5/2020 | Dellinger |
| 2020/0170963 A1 | 6/2020 | Tich et al. |
| 2020/0188324 A1 | 6/2020 | Sebree et al. |
| 2020/0188348 A1 | 6/2020 | Sinai et al. |
| 2020/0206184 A1 | 7/2020 | Robson et al. |
| 2020/0214995 A1 | 7/2020 | Sebree et al. |
| 2020/0215136 A1 | 7/2020 | Naheed |
| 2020/0237683 A1 | 7/2020 | Whalley et al. |
| 2020/0253919 A1 | 8/2020 | Raz et al. |
| 2020/0261376 A1 | 8/2020 | Yu et al. |
| 2020/0261404 A1 | 8/2020 | Raz et al. |
| 2020/0276132 A1 | 9/2020 | Weimann |
| 2020/0297656 A1 | 9/2020 | Guy et al. |
| 2020/0330379 A1 | 10/2020 | Singh et al. |
| 2020/0338041 A1 | 10/2020 | Smith et al. |
| 2020/0338151 A1 | 10/2020 | Witowski et al. |
| 2020/0345653 A1 | 11/2020 | Hansen et al. |
| 2020/0345655 A1 | 11/2020 | Heinzerling et al. |
| 2020/0345657 A1 | 11/2020 | Lurya et al. |
| 2020/0345685 A1 | 11/2020 | Otiko |
| 2020/0352849 A1 | 11/2020 | Rotunda |
| 2020/0352901 A1 | 11/2020 | Raber et al. |
| 2020/0360299 A1 | 11/2020 | Bonn-Miller et al. |
| 2020/0384048 A1 | 12/2020 | Kariman |
| 2020/0384049 A1 | 12/2020 | Kariman |
| 2021/0015740 A1 | 1/2021 | Greenspan |
| 2021/0023044 A1 | 1/2021 | Spirtos |
| 2021/0023045 A1 | 1/2021 | Raz et al. |
| 2021/0030777 A1 | 2/2021 | Maida |
| 2021/0052512 A1 | 2/2021 | Guy et al. |
| 2021/0052545 A1 | 2/2021 | Jones, Jr. et al. |
| 2021/0059976 A1 | 3/2021 | Wilkhu et al. |
| 2021/0069333 A1 | 3/2021 | Velasco Diez et al. |
| 2021/0077421 A1 | 3/2021 | Sebree et al. |
| 2021/0100737 A1 | 4/2021 | Plakogiannis et al. |
| 2021/0106540 A1 | 4/2021 | Plakogiannis et al. |
| 2021/0113489 A1 | 4/2021 | Plakogiannis et al. |
| 2021/0137833 A1 | 5/2021 | Wang et al. |
| 2021/0145764 A1 | 5/2021 | Lephart |
| 2021/0186860 A1 | 6/2021 | Weimann |
| 2021/0196669 A1 | 7/2021 | Bar-Lev Schleider et al. |
| 2021/0236417 A1 | 8/2021 | Plakogiannis et al. |
| 2021/0244680 A1 | 8/2021 | Kassab |
| 2021/0244683 A1 | 8/2021 | Chaiyasate |
| 2021/0244684 A1 | 8/2021 | Ghalili et al. |
| 2021/0251918 A1 | 8/2021 | Plakogiannis et al. |
| 2021/0259989 A1 | 8/2021 | Plakogiannis et al. |
| 2021/0290565 A1 | 9/2021 | Guy et al. |
| 2021/0308070 A1 | 10/2021 | Summers |
| 2021/0308072 A1 | 10/2021 | Wright et al. |
| 2021/0346310 A1 | 11/2021 | Plakogiannis et al. |
| 2021/0379011 A1 | 12/2021 | Guynn |
| 2021/0386684 A1 | 12/2021 | Weimann |
| 2021/0386685 A1 | 12/2021 | Weimann |
| 2021/0401766 A1 | 12/2021 | Rhodes et al. |
| 2021/0401770 A1 | 12/2021 | Fracassi et al. |
| 2021/0401771 A1 | 12/2021 | Guy et al. |
| 2022/0000794 A1 | 1/2022 | Plakogiannis et al. |
| 2022/0047525 A1 | 2/2022 | Plakogiannis et al. |
| 2022/0062211 A1 | 3/2022 | Stott et al. |
| 2022/0347151 A1 | 11/2022 | Plakogiannis et al. |

FOREIGN PATENT DOCUMENTS

| | | |
|---|---|---|
| WO | 2004016246 | 2/2004 |
| WO | 2006041841 | 4/2006 |
| WO | 2006044645 | 4/2006 |
| WO | 2008021394 | 2/2008 |
| WO | 2008024408 | 2/2008 |
| WO | 2008024490 | 2/2008 |
| WO | 2008039179 | 4/2008 |
| WO | 2008063625 | 5/2008 |
| WO | 2008129258 | 10/2008 |
| WO | 2009020666 | 2/2009 |
| WO | 2009131794 A1 | 10/2009 |
| WO | 2010126501 | 11/2010 |
| WO | 2010126501 A1 | 11/2010 |
| WO | 2010127033 | 11/2010 |
| WO | 2011026144 A1 | 3/2011 |
| WO | 2013088135 A1 | 6/2013 |
| WO | 2013108254 | 7/2013 |
| WO | 201314902 A1 | 10/2013 |
| WO | 2014020155 A1 | 2/2014 |
| WO | 2015025312 | 2/2015 |
| WO | 2015031410 A1 | 3/2015 |
| WO | 2016073653 A1 | 5/2016 |
| WO | 2016141056 A1 | 9/2016 |
| WO | 2018071581 | 4/2018 |
| WO | 2018135943 | 7/2018 |
| WO | 2019058261 | 3/2019 |
| WO | 2019130215 | 7/2019 |
| WO | 2019210287 | 10/2019 |
| WO | 2020016581 | 1/2020 |
| WO | 2020016582 | 1/2020 |
| WO | 2020053857 | 3/2020 |
| WO | 2020115751 | 6/2020 |
| WO | 2020123625 | 6/2020 |
| WO | 2020136593 | 7/2020 |
| WO | 2020136627 | 7/2020 |
| WO | 2020142692 | 7/2020 |
| WO | 2020152438 | 7/2020 |
| WO | 2020157569 | 8/2020 |
| WO | 2020157639 | 8/2020 |
| WO | 2020181295 | 9/2020 |
| WO | 2020183350 | 9/2020 |
| WO | 2020198252 | 10/2020 |
| WO | 2020198883 | 10/2020 |
| WO | 2020220092 | 11/2020 |
| WO | 2021003341 | 1/2021 |
| WO | 2021003467 | 1/2021 |
| WO | 2021023351 | 2/2021 |
| WO | 2021050429 | 3/2021 |
| WO | 2021055499 | 3/2021 |
| WO | 2021070120 A1 | 4/2021 |
| WO | 2021102353 | 5/2021 |
| WO | 2021177937 | 9/2021 |
| WO | 2021177940 | 9/2021 |
| WO | 2021214544 A1 | 10/2021 |
| WO | 2021236782 | 11/2021 |
| WO | 2022118290 A1 | 6/2022 |

OTHER PUBLICATIONS

International Search Report for PCT/IB2022/053271 mailed Jul. 12, 2022.
Smith, Eric W, "Percutaneous Penetration Enhancesrs" CRC Press, ISBN:0849326052.
Grodowska, Katarzyna, "Organic Solvents in the Pharmaceutical Industry", Acta Pol Pharm, Jan.-Feb. 2010; vol. 67, pp. 3-12.
Carhart-Harris, R.L., Psilocybin with psychological support for treatment-resistant depression: six-month follow up, vol. 235(2), pp. 399-408, 2018, Psychopharmacology.
Fadiman, James et al., "Might Microdosing Psychedelics Be Safe and Beneficial? An Initial Exploration", Journal of Psychoactive Drugs, 2018, pp. 118-122, vol. 51(2), https: www.tandfonline.com/lol/ujpd20.

(56) References Cited

OTHER PUBLICATIONS

Andersson, Martin, "Psychoactive substances as a last resort—a qualitative study of self treatment of migraine and cluster headaches", Harm Reduction Journal, vol. 14(1), pp. 1-10, 2017.
Cameron, Lindsay P. et al., "Psychedelic Microdosing: Prevalence and Subjective Effects" Journal of Psychoactive Drugs, , 2020, pp. 113-122, vol. 52(2).
Alper, Kenneth R. et al., "The ibogaine medical subculture" Journal of Ethsopharmacology, 2008, pp. 9-24, vol. 115(1).
Glick, Stanley et al., "18-Methoxycoronaridine (18-MC) and Ibogaine: Comparison of Antiaddictive Effiacy Toxicity, and Mechanisms of Action" Annals of the New York Academy of Sciences, 2006, pp. 369-386, vol. 914(1).
Politio, Vince, "A systematic study of microdosing psychedelics", PLOS One, 2019, pp. 1-26, vol. 14(2).
Beug, Michael W. et al., "Psilocybin and Psilocin Levels in Twenty Species From Seven Genera of Wild Mushrooms in the Pacific Northwest, U.S.A." Journal of Ethnopharmacology, 1982, pp. 271-285, vol. 5(3).
Sinha, V.R. et al., "Permeation Enhancers for Transdermal Drug Delivery" Drug Development and Industrial Pharmacy, pp. 1131-1140, vol. 26.
Barkan, S., et al. (2014), "A double-blind, randomised, placebo-controlled trial of oral midazolam plus oral ketamine for sedation of children during laceration repair." Emerg Med J 31(8): 649-653.
Jennings, C. A., et al.(2013) "Oral ketamine for sickle cell crisis pain refractory to opioids." J Pain Palliat Care Pharmacother 27(2): 150-154.
Peter Sos, M.K. Tomas Novak, Barbra Kohutova, Jiri Horacek, Tomas Palenicek (2013). "Relationship of ketamine's antidepressant and psychomimetic effectsi n unipolar depression." Activitas Nervosa Superior Rediviva 34(4): 287-293.
Permoda-Osip, A., et al. (2013). "Vitamin B12 level may be related to the efficacy of single ketamine infusion in bipolar depression." Pharmacopsychiatry 46(6): 227-228.
Segmiller, F., et al. (2013). "Repeated S-ketamine infusions in therapy resistant depression: a case series." J Clin Pharmacol 53(9): 996-998.
Yoosefi, A., et al.(2014). "Comparing effects of ketamine and thiopental administration during electroconvulsive therapy in patients with major depressive disorder, a randomized, double-blind study." J Ect 30(1): 15-21.
Ghasemi M., et al., (2014), Rapid antidepressant effects of repeated doses of ketamine compared ith electroconvulsive therapy in hospitalized patients with major depressive disorder, "Psychiatry Res 215(2): 355-361."
Rasmussen, K. G., et al.(2014), "A randomize comparison of ketamine versus methohexital anesthesia in electroconvulsive therapy." Psychiatry res 215(2): 362-365.
De Gioannis, A. and D. De Leo (2014), "Oral ketamine augmentation for chronic suicidality in treatment-resistant depression." Aust N Z J Psychiatry 48(7): 686.
Lai, R., et al. (2014) "Pilot dose-response trial of i.v. ketamine in treatment-resistant depression." World J Biol Psychiatry 15(7): 579-584.
Moaddel, R., et al.(2015), "-serine plasma concentration is a potential biomarker of (R, S)-ketamine antidepressant response in subjects with treatment-resistant depression." Psychopharmacology (Berl) 232(2): 399-409.
Erdil, F., et al.(2015). Effects of sevoflurane or ketamine on the QTc interal during electroconvulsive therapy. J Anesth 29(2): 180-185.
Amin, P., et al.(2014) "Case report: efficacy and tolerability of ketamine in opioid-refractory cancer pain," J Pain Palliat Care Pharmacother 28(3): 233-242.
Ionescu, D. F., et al.(2014) "Effect of baseline anxious depression on initial and sustained antidepressant response to ketamine." J Clin Psychiatry 75(9): e932-938.
Permoda-Osip, A., et al. (2015) "single ketamine infusion and neurocognitive performance in bipolar depression.", Pharmacopsychiatry 48(2): 78-79.

Marchetti, F., et al.(2015), "Efficacy and safety of oral ketamine for the relief of intractable chronic pain: A retrospective 5-year study of 51 patients." Eur J Pain 19(7): 984-993.
Koksai, P.M. and M. Gurbuzel (2015). "Analysis of genotoxic activity of ketamine and rocuronium bromide using the somatic mutation and recombination test in Drosophila melanogaster." Environ Toxicol Pharmacol 39(2): 628-634.
Preskorn, S., et al. (2015). "Randomized proof of concept trial of GLYX-13, an N-methyl-D-aspartate receptor glycine site partial agonist, in major depressive disorder nonresponsive to a previous antidepressant agent." J Psychiatr Pract 21(2): 140-149.
Afsaneh Norouzi et al (2015). "Comparison of the Effects of oral vs. peritonsillar infiltration of ketamine in pain reduction after tonsillectomy: a randomized Clinical trial" M.E.J. Anesth 23(1).
Murrough, J.W, et al. (2015) "Ketamine for rapid reduction of suicidal ideation: a randomized controlled trial." Psychol Med 45(16): 3571-3580.
Leffa, D.D., et al.(2016). "Anesthetic Ketamine-Induced DNA Damage in Different Cell types In vivo." Mol Neurobiol 53(8): 5575-5581.
Hu, Y.D., et al.(2016) Single i.v. ketamine augmentation of newly initiated escitalopram for major depression: results from a randomized, placebo-controlled 4-wekk study. Psychol Med 46(3): 623-635.
Li, C.T et al.(2016). "The effects of low-dose ketamine on the prefrontal cortex and amygdala in treatment-resistant depression: A randomized controlled study." Hum Brain Mapp 37(3): 1080-1090.
Singh, J.B., et al.(2016). "A Double-Blind, Randomized, Placebo-Controlled, Dose-Frequency Study of Intravenous Ketamine in Patients with Treatment-Resistant Depression." A J Psychiatry 173(8): 816-826.
Jafarinia, M., et al (2016). "Efficacy and safety of oral ketamine versus diclofenac to alleviate mild to moderate depression in chronic pain patients: A double-blind, randomized, controlled trial." J Affect Disord 204: 1-8.
Swiatek, K.W., et al.(2016) "New use for an old drug: oral ketamine for treatment-reistant depression." BMJ Case Rep 2016.
Rao, L.K. et al.(2016). "Role of Cytochrome P4502B6 Polymorphisms in Ketamine Metabolism and Clearance." Anesthesiology 125(6): 1103-1112.
Papadiitropouou, K., et al.(2017). "Comparatie efficacy and tolerability of pharmacoloical and somatic interventions in adult patients with treatment-resistant depression: a systematic review and network meta-analysis." Curr Med Res Opin 33(4): 701-711.
Grande, L., et al.(2016) "(417) Oral ketamine for chronic pain: a 32-subject placebo-controlled trial in patients on chronic opioids." The Journal of Pain 17(4): S78-S79.
Shillingburg, A., et al.(2017) "Treatment of Severe mucositis pain with oral ketamine mouthwash." Support Care Cancer 25(7): 2215-2219.
Al Shiraw, M.I., et al.(2017). "Oral Ketamine in Treatment-Resistant Depression: A Clinical Effectiveness Case Series." J Clin Psychopharmacol 37(4): 464-467.
Conway, et al. Toward an Evidence-Based, Operational Definition of Treatment-Resistant Depression, When Enough s Eough, JAWA Psychiatry, Jan. 2017, vol. 74, No. 1, pp. 9-10.
Lucie Bartova, A.W, Markus Dold, Angela Naderi-heiden, Siegfred Kasper, Matthaeus Willeit, Nicole Praschak-Rieder, (2017) "Robust Antidepressant Effect Following Alternating Intravenous Racemic Ketamine and Electroconvulsive therapy in Treatment-Resistant Depression: A Case Report." Journal of ECT 00(00).
Zhao, W., et al.(2017). "Self-Assembled ZnO Nanoparticle Capsules for Carrying and Delivering Isotretinoin to Cancer Cells." ACS Appl Mater Interfaces 9(22): 18474-18481.
Robert M. Berman, A.C., Amit Anand, Dan A. Oren, George R. Heninger, Dennis S. Charney, and John H. Krystal (2000). "Antiepressant Effects of Ketamine in Depressed Patients." Sciety of biological Psychiatry 47: 351-354.
Baker, S.C., et al.(2016). "Ketamine-Inuced Apoptosis in Normal Human Urothelial Cells: A Direct, N-Methyl-d-Aspartate Receptor-Independent Pathway Characterized by Mitochondrial Stress." Am J Pathol 186(5): 1267-1277.

(56) References Cited

OTHER PUBLICATIONS

Beaudoin, F. L., et al.(2014) "Low-dose ketamine improves pain relief in patients receiving intravenous opioids for acute pain in the emergency department results of a randomized, double-blind, clinical trial." Acad Emerg Med 21(11): 1193-1202.
Boulieu, S.B. a.R. (1998) "HPLC determination of ketamine, norketamine, and dehydronorketamine in plasma with a high-purity reversed-phase sorbent." Clinical Chemistry 44(3) 560-564.
Wang, C., et al.(2013) "Brain damages in ketamine addicts as revealed by magnetic resonance imaging." Front Neuroanat 7: 23.
Bredlau, A.L., et al.(2013) "Oral ketamine for children with chronic pin, a pilot phase 1 study." J Pediatr 163(1): 194-200 e 191.
J. Douglas Bremmer, J. H. K. Frank W. Putnam, Steen M. Southwick, Charles Marmar, Dennis S. Charneyand Carolyn M. Mazure (1998). "Measrement of sisociative States with the Clinician-Administered Dissociative States Scale (CADSS)." Journal of Traumatic Stress 111).
Brooks, M. (2016) "Repeated Ketamine May sustain Antidepressant Effect." American Journal of psychiatry.
Brown, et al, Treatment Outcomes for primary Care patients with major Depression and Lifetime Anxiety Disorders, Am J Psychiatry 153: 10, Oct. 1996.
Loo CK, et al., Placebo-controlled pilot trial testing dose titration and intravenous, intramuscular and subcutaneous routes for ketamine in depression, Acta Psychiatr Scand, Jul. 2016; 134(1) 48-56, dol: 10, 111/acps. 12572, Epub Mar. 30, 2016.
Viberg, et al, Neonatal ketamine exposure results in changes in biochemical substrates of neuronal growth and synaptogenesis, and alters adult behavior irreversibly, Toxicology 249 (2008) 153-159.
Carliss, et al., oral adminitration of dextromethorphan does not produce neuronal vacuolation in the rat brain ScienceDirect Neuro toxicology 28 (2007) 813-818.
Zhao, W., et al Ketamne administered to pregnant rats in the second trimester causes long-lasting behavioral disorders in offspring, Neurobiology of Disease 68 (2014) 145-155.
Zhang, et al, Reactive Oxygen Species-mediated Loss of of Phenotype of Parvalbumin Interneurons Contributes to Longterm Cognitive Impairments After Repeated Neonatal ketamine Exposures, Neurotox Res (2016) 30:593-605.
Center for Drug Evaluation and Research, Application No. 210365Orig1s000; Non Clinical Reviews; Submission date: Jun. 23, 2017.
Leehy, M et al., "Safety and Tolerability of Cannabidiol in Parkinson's Disease: An Open Label, Dose-Escalation Study, Cannabis and Cannabinoid Research", 2020, vol. 5, No. 4.
McPartland, J et al., "Care and Feeding of the Endocannabinoid System: A Systematic Review of Potential Clinical Interventions that Upregulate the Endocannabinoid System". PLOS One, Mar. 12, 2014, vol. 9, Issue 3.

Ohlsson, Per-Ingvar, "Lacetoperoxidase, a dithionite ion dismutase" Eur. J. Biochem, 1984, vol. 142, pp. 233-238.
Shapiro, L., "Children, but Linked to Side Effects Analysis: Clinicians should consider adverse effects before treatment", Dravet Syndrome News, Aug. 30, 2022.
Taylor, L. "A Phase I, Randomized, Double-Blind, Placebo-Controlled, Single Ascending Dose, Multiple Dose and Food Effect Trial of the Safety, Tolerability and Pharmacokinetics of Highly Purified Cannabidiol in Healthy Subjects", CNS Drugs, 2018, vol. 32, pp. 1053-1067.
International Preliminary Report on Patentability for International Application No. PCT/IB2022/053271 dated Oct. 19, 2023.
Schalau, G.K. et al. "Silicone Adhesives in Medical Applications. Applied Adhesive Bonding in Science and Technology", Edited by Halil Özer. Published: Dec. 20, 2017. DOI: 10.5772/intechopen. 71817.
SYLOID® Silica Excipients. Pharmaceutical and Nutraceutical Solutions. W. R. Grace & Co. 2020. https://grace.com/products/syloid-silica/.
Brown, P. "Tertiary Pharmacology Review", 2017.
Extended European Search Report for European Application No. 20875154.5 dated Jan. 3, 2024.
International Report on Patentability for International Application No. PCT/IB2022/053271 dated Oct. 19, 2023.
CN108785298 Zhang et al. "A kind of pharmaceutical composition, preparation method and the usage for treating epilepsy." Machine Translation. Nov. 13, 2018.
International Search Report for PCT/IB2020/059482 dated Jan. 28, 2021.
IP Australia Examination Report for AU Application No. 2020361741 dated Jun. 19, 2024.
Silvestro, S. et al. Use of Cannabidiol in the Treatment of Epilepsy: Efficacy and Security in Clinical Trials. Molecules. Apr. 12, 2019;24(8):1459.
Hammell, D.C. et al. Transdermal cannabidiol reduces inflammation and pain-related behaviours in a rat model of arthritis. Eur J Pain. Jul. 2016 ; 20(6): 936-948.
Franco, V. et al. Pharmacological and Therapeutic Properties of Cannabidiol for Epilepsy. Drugs. Sep. 2019;79(13):1435-1454.
ASI. "Adhesives in Transdermal Drug Delivery Systems." Nov. 1, 2005.
International Preliminary Report On Patentability for PCT/IB2020/059482 dated Apr. 12, 2022.
Written Opinion of the International Searching Authority for or PCT/IB2020/059482 dated Jan. 29, 2021.
Office Action for Japanese Patent Application No. 2012-525416 issued on Jul. 2, 2024 (includes English language translation).

\* cited by examiner

PHARMACEUTICAL COMPOSITION AND METHOD FOR TREATING SEIZURE DISORDERS

This application claims priority to U.S. Ser. No. 62/913,874, filed Oct. 11, 2019, the entirety of which is incorporated herein by reference.

BACKGROUND

The present disclosure relates to the transdermal administration of cannabidiol (CBD) for the reduction of seizure frequency in the treatment of, for example, "treatment-resistant epilepsy" (TRE), including treatment resistant pediatric epilepsy, or Tuberous Sclerosis Complex (TSC), Dravet Syndrome and Lennox-Gastaut Syndrome. In one embodiment the patients suffering from TRE are children and young adults. CBD appears particularly effective when the TRE is Dravet syndrome; myoclonic absence seizures or febrile infection related epilepsy syndrome (FIRES). In these indications the reduction of total convulsive frequency has surprisingly been shown to be greater than 50%, through 70% to greater than 90% in a significant number of patients. Indeed a significant number of patients have been seizure free at the end of three months treatment.

Preferably the CBD used is in the form of a highly purified extract of cannabis such that the CBD is present at greater than, for example, 98% of the total extract (w/w) and the other components of the extract are characterised. In particular tetrahydrocannabinol (THC) has been substantially removed to a level of not more than, for example, 0.15% (w/w). Alternatively, it is a synthetically produced CBD (See U.S. Pat. No. 10,195,159).

The CBD may be used concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner Cannabis (marijuana) is a schedule-I drug in USA. Cannabis is a flowering plant which contains more than 400 phytonutrient (micronutrient). More than 100 different types of terpenoids, essential oils, antioxidants and cannabinodis have been extracted from the plant. From all of the phytochemicals, only tetryhydrocannbinol (THC) showed significant psychoactive effect. A number of research papers have been published on THC due to its psychoactive and therapeutic effects. Apart from THC, several other constituents have been studied, which also showed some therapeutic effect without psychoactive effect such as cannabidiol (CBD), cannbinol (CBN), cannabichromene (CBC), cannabigerol (CBG), tetrahydrocannbivarin (THCV), delta 9-tetrahydrocannbinol (delta9THC) and many more. It has been showed that cannabis and its derivatives can be used for the treatment of pain, antimicrobial, type-2 related metabolic disorder, decrease intraocular pressure, Dravet syndrome, Lennox-Gastaut Syndrome (LGS), epilepsy, nausea, pain and wasting associated with AIDS, arthritis and rheumatism, migraines, muscle spasticity associated with multiple sclerosis and paralysis, alcohol and narcotics withdrawal, stress and depression, asthma, fibromyalgia, inflammatory pain, and pain and/or inflammation associated with chemotherapy. FDA approved Marinol and Syndros contains delta 9-THC, which currently using in pain and/or inflammation associated with chemotherapy treatments. Furthermore, in April 2016 FDA gave orphan drug designation to cannabidiol for the treatment of Tuberous Sclerosis Complex (TSC), Dravet Syndrome and Lennox-Gastaut Syndrome.

Lennox-Gastaut Syndrome (LGS) is a severe form of epilepsy that typically becomes apparent during infancy or early childhood. Onset of LGS is usually between 2-7 years with a peak onset between 3 to 5 years. Affected Children experience several different types of seizures most commonly atonic, tonic and atypical absence seizures.

In 2018, GW Pharmaceutical received FDA approval for its fast track designated drug "Epidiolex" (Cannabidiol) to treat two orphan conditions in children-LGS and Dravet syndrome (DS).

Epidiolex contains naturally derived cannabidiol from Sativex plant in oral solution form (100 mg/ml). According to the FDA Label, the recommended dose of Epidiolex described in Table 1.

TABLE 1

Recommended dose of Epidiolex for LGS and DS[1]

| Recommended Dose | Avg wt of 2 years old Child (kg) | Avg wt of 7-year-old Child (kg) | Total Dose (2-7 yrs) |
|---|---|---|---|
| 5 mg/kg/day | 12.25 | 22.7 Kg | 61.25-113.5 mg/day |
| 10 mg/kg/day | (12-12.5 kg) | (22.4-22.9 Kg) | 122.5-227 mg/day |
| 20 mg/kg/day | | | 245-454 mg/day |

Epidiolex has mainly five dose dependent side effects: 1) Hepatocellular injury, 2) Somnolence and sedation, 3) Suicidal Behavior and Ideation, 4) Hypersensitivity Reaction and 5) withdrawal of antiepileptic drugs[1].

The discontinuation rate of Epidiolex is high due to hepatocellular injury and somnolence and sedation side effects. During clinical trial 1.3% patient taking 10 mg/kg/day and 5.9% patient taking 20 mg/kg/day Epidiolex discontinue due to hepatocellular injury. Furthermore, there were 0% patient taking dose of 10 mg/kg/day and 3% patient taking 20 mg/kg/day dropped out due to somnolence and sedation. Table 2 provides the dose dependent side effects due to Epidiolex[1].

TABLE 2

Dose dependent Adverse effects: (FDA)[1]

| | EPIDIOLEX | | |
|---|---|---|---|
| Adverse Reactions | 10 mg/kg/day N = 75 % | 20 mg/kg/day N = 238 % | Placebo N = 227 % |
| Hepatic Disorders | | | |
| Transaminases elevated | 8 | 16 | 3 |
| Hepatocellular Injury | 1 | 17 | 0 |
| Gastrointestinal Disorders | | | |
| Decreased appetite | 16 | 22 | 5 |
| Diarrhea | 9 | 20 | 9 |
| Weight decreased | 3 | 5 | 1 |
| Gastroenteritis | 0 | 4 | 1 |
| Abdominal pain, discomfort | 3 | 3 | 1 |
| Nervous System Disorders | | | |
| Somnolence | 23 | 25 | 8 |
| Sedation | 3 | 6 | 1 |

TABLE 2-continued

Dose dependent Adverse effects: (FDA)[1]

| Adverse Reactions | EPIDIOLEX | | |
| --- | --- | --- | --- |
| | 10 mg/kg/day N = 75 % | 20 mg/kg/day N = 238 % | Placebo N = 227 % |
| Lethargy | 4 | 8 | 2 |
| Fatigue, malaise, asthenia | 11 | 12 | 4 |
| Insomnia, sleep disorder, poor quality sleep | 11 | 5 | 4 |
| Irritability, agitation | 9 | 5 | 2 |
| Aggression, anger | 3 | 5 | <1 |
| Drooling, salivary hypersecretion | 1 | 4 | <1 |
| Gait disturbance | 3 | 2 | <1 |
| Infections | | | |
| Infection, all | 41 | 40 | 31 |
| Infection, viral | 7 | 11 | 6 |
| Pneumonia | 8 | 5 | 1 |
| Infection, fungal | 1 | 3 | 0 |
| Infection, other | 25 | 21 | 24 |
| Other | | | |
| Rash | 7 | 13 | 3 |
| Hypoxia, respiratory failure | 3 | 3 | 1 |

These side effects are dose related and therefore it is required to monitor the patients and reduced the dose if needed. However, the TDDS system is delivering the drug molecule constantly at defined input rate. Instead of peaks and valley in plasma concentrations like in oral delivery, the TDDS maintain the average plasma concentration at predetermined constant input rate.

While there are patents available on cannabidiol, the shortcomings of these disclosures are overcome by the disclosure herein. For example, U.S. Pat. No. 9,375,417 fails to provide any in-vitro or in-vivo data. U.S. Pat. No. 6,328,992 discloses reservoir and adhesive matrix patches, however, these examples contain mixture of cannabinoids (such as delta-8-THC, delta-9-THC, cannabidiol, and cannabinol) instead of cannabidiol only. The THC is a psychoactive agent and an addictive substance, so the utility is problematic.

In addition, U.S. Pat. No. 8,449,908 discloses delivery of the cumulative amount of 60600 ng in 48 hrs through the human cadaver skin. This amount represents the flux of 1925 ng/sqcm/hr. The patch area can be calculated using following equation.

$$\text{In-Vitro Flux (ug/sqcm/hr)} = (C_{ss} \text{(ug/l)} * CL \text{(L/Hr)}) / \text{Patch Area (Sqcm)}$$

$$\text{Patch Area (Sqcm)} = (C_{ss} \text{(ug/l)} * CL \text{(L/hr)}) / \text{In-Vitro Flux (ug/sqcm/hr)}$$

$$= (10 * 74.4) / 1.925$$

$$= 386 \text{ sqcm}$$

In order to deliver 5 mg/kg/day cannabidiol, the patient has to apply formulation on 386 sqcm surface area. This is an impractical patch size for any Transdermal drug delivery system (TDDS). Furthermore, the '908 patent discloses using receiving media PBS:PEG-400 (60:40). It is very well known that PEG-400 is permeability enhancer and by incorporating it in receiving media, the skin is damaged from the dermis side, this can also increase the permeation amount due to unviable skin samples.

There is a need for an improved drug delivery system of cannabidiol which can overcome the drawbacks associated with oral and IV route. Transdermal delivery of highly purified cannabidiol can address the challenges associated with oral and IV drug delivery. The current invention addresses all the above drawbacks and provides a real world utility. Furthermore, the current disclosed herein is the use of a synthetic version of cannabidiol which is manufactured in more controlled environment than the botanical source of the same. The synthetic version of cannabidiol provides more permeability as compared to adulterated versions of it. Moreover, the disclosure is directed to, for example, transdermal matrix patches which can deliver synthetic cannabidiol for 1 day, and/or 2-days, and/or 3-days, and/or 4 days, and/or 5 days, and/or 6 days, and/or 7 days, and/or up to 15 days.

All references cited herein are incorporated herein by reference in their entireties.

BRIEF SUMMARY

The disclosure provides compositions and methods for the treatment and/or prevention and/or control of seizure disorders, using transdermal drug delivery. In Transdermal drug delivery, a transdermal patch or transdermal composition is applied topically to the skin surface. Throughout the duration of topical application of a transdermal patch or transdermal composition drug is continuously released and delivered through the intact skin (via transcellular, intercellular and transappendageal routes) to achieve systemic effect. Therefore, once applied transdermal composition or transdermal patch can deliver drug into systemic circulation throughout the day or even for more than one day depending on the duration of its application which can be even up to a week.

Transdermal delivery can reduce the dosing frequency of CBD which is currently administered several times a day. Through transdermal delivery, transdermal compositions or transdermal formulations or transdermal patch of highly purified CBD, can be applied topically to skin thereby delivering the drug throughout the duration of topical application. Depending on the requirement, the duration of topical application can be once in a day, once in two days, once in three days, once in four days, once in five days, once in a week. Therefore, transdermal delivery can overcome the multiple dose regimen of oral delivery by reducing the dosing frequency.

Moreover, in transdermal drug delivery the drug is delivered slowly and continuously throughout the duration of topical application hence there are no peaks and troughs in drug plasma concentration which are associated with multiple dose administration in a day. Therefore, by transdermal delivery of highly purified CBD, patients can have the therapeutic effect of the drug for extended period of time without drastic changes in drug plasma concentration.

In transdermal delivery drug is delivered into systemic circulation through the skin, it escapes the first pass hepatic metabolism therefore to achieve the desired therapeutic activity less drug is required, resulting into less adverse effects or side effects. Cannabinol has high lipid solubility and after oral administration undergoes hepatic first pass metabolism, therefore of the administered dose only 10%-20% reaches systemic circulation, thus as compared to oral dose, transdermal delivery a small dose of cannabidiol can give the desired therapeutic effects at a lower dose than oral.

Furthermore, transdermal delivery is easy, noninvasive and convenient. Administration of a transdermal patch or transdermal composition does not require medical supervision as patients can topically apply the transdermal patch or transdermal composition themselves. Therefore, transdermal delivery can overcome the drawbacks of injections which are often painful and requires medical supervision.

With respect to cannabidiol it is expected that interpatient variability in pharmacologic response will be less with transdermal delivery as drug plasma concentration can be controlled by controlling the rate of drug delivery from transdermal composition or transdermal patch. With transdermal delivery a small amount of cannabidiol can be delivered for longer duration than oral administration. Transdermal formulations of cannabidiol also provide more abuse deterrence than immediate release dosage forms.

Moreover, in case of any adverse effect, side effect or emergency transdermal delivery gives the liberty to terminate the therapy anytime by taking off the transdermal patch or transdermal composition from skin.

As per above stated reasons for the treatment and/or prevention and/or control of seizure disorders, transdermal delivery can provide patient friendly, simplified and convenient therapeutic regimen over traditional delivery systems. Transdermal delivery can reduce the dosing frequency of highly purified CBD. Depending on the necessity, dosing frequency can be once in a day, once in two days, once in three days, once in four days, once in five days, once in six days, once in a week.

Through transdermal administration of drug combination, two or more drugs can be delivered simultaneously. Depending on the necessity, dosing frequency of transdermal patch or transdermal composition containing drug combination can be once in a day, once in two days, once in three days, once in four days, once in five days, once in six days, once in a week. It would be a great addition to the patient compliance.

The disclosure provides a pharmaceutical composition comprising at least about 90% (w/w) cannabidiol (CBD), in a dosage form for transdermal delivery. The disclosure provides a pharmaceutical composition which comprises at least about 95% CBD. The disclosure provides a pharmaceutical composition which comprises at least about 98% CBD. The disclosure provides a pharmaceutical composition which comprises at least about 99% CBD. The disclosure provides a pharmaceutical composition formulated as transdermal liquid formulation, transdermal semisolid formulation, or transdermal polymer matrix formulation. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, and combinations thereof. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, and combinations thereof in the range of 0.01%-95% w/w or w/v. The disclosure provides a pharmaceutical composition wherein the carrier is present in the range of 0.01%-99.8% w/w or w/v. The disclosure provides a pharmaceutical composition which is formulated as a transdermal patch. The disclosure provides a pharmaceutical composition formulated as a transdermal patch, wherein the transdermal patch is selected from the group such as to reservoir patch, a microreservoir patch, a matrix patch, a pressure sensitive adhesive patch, extended release transdermal film a liquid reservoir system, a microreservoir patch, a matrix patch, a pressure sensitive adhesive patch, a mucoadhesive patch, and combinations thereof. The disclosure provides a pharmaceutical composition indicated for the treatment and/or prevention and/or control of seizure disorder in a patient, wherein the seizure disorder disorders include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, mesial temporal lobe epilepsy, nocturnal frontal lobe epilepsy, progressive epilepsy with mental retardation, and progressive myoclonic epilepsy, as well as seizures associated with CNS mass lesions. The disclosure provides a pharmaceutical composition which is formulated as the transdermal formulation which can be administered in a dosage regimen selected from the group consisting of once daily, twice daily, three times a day, once in 1-8 hrs, once in 1-24 hrs, once in two days, once in three days, once in four days, once in five days, once in six days, once in a week, once in a 8 to about 13 days, once in two weeks, once in 15 days to about 30 days. The disclosure provides a pharmaceutical composition which may be formulated as microneedles. The disclosure provides a pharmaceutical composition wherein said CBD or derivative thereof is produced by a synthetic route. The disclosure provides a pharmaceutical composition co-administered with at least one additional an anti-epileptic agent selected from the group consisting of: clobazam; levetiracetam; topiramate; stiripentol; phenobarbital; lacsamide; valproic acid; zonisamide; perampanel; and fosphenytoin. The disclosure provides a pharmaceutical composition further comprising at least one additional an anti-epileptic agent selected from the group consisting of: clobazam; levetiracetam; topiramate; stiripentol; phenobarbital; lacsamide; valproic acid; zonisamide; perampanel; and fosphenytoin.

The disclosure provides a method for the treatment and/or prevention and/or control of seizure disorder in a patient comprising: selecting a patient in need of treatment and/or prevention and/or control of seizure disorder; topically applying the pharmaceutical composition as disclosed herein. The disclosure provides a method for the treatment and/or prevention and/or control of seizure disorder in a patient wherein the seizure disorder includes complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, mesial temporal lobe epilepsy, nocturnal frontal lobe epilepsy, progressive epilepsy with mental retardation, and progressive myoclonic epilepsy, as well as seizures associated with CNS mass lesions. The disclosure provides a method for the treatment and/or prevention and/or control of seizure disorder in a patient wherein the topical application of a transdermal patch for the treatment and/or prevention and/or control of seizure disorder in a patient, wherein the seizure disorder include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, mesial temporal lobe epilepsy, nocturnal frontal lobe epilepsy, progressive epilepsy with mental retardation, and progressive myoclonic epilepsy, as well as seizures associated with CNS mass lesions is selected from the group consisting of once in a day, once in two days, once in three days, once in four days, once in five days, once in six days, once in a week, once in ten days. The disclosure provides a method for the treatment and/or prevention and/or control of seizure disorder in a patient further providing a constant rate of delivery of the active components of the transdermal patch over a time period. The disclosure provides a method for the treatment and/or prevention and/or control of seizure disorder in a patient further providing a steady absorption rates of the active components of the transdermal patch over a time period. The disclosure provides a method for the treatment and/or prevention and/or control of seizure disorder in a patient further achieving a constant blood serum levels of the active components of the transdermal patch over a time period. The disclosure provides a method for the treatment and/or prevention and/or control of seizure disorder in a patient further achieving a reduced variability in dosage of the active components of the transdermal patches over a time period. The disclosure provides a method for the treatment and/or prevention and/or control of seizure disorder in a patient further providing a plasma concentration of the active components of the transdermal patch in a therapeutic range over a period of time.

The disclosure provides a pharmaceutical composition comprising a highly purified extract of cannabis which comprises at least about 90% (w/w) cannabidiol (CBD), in a dosage form for transdermal delivery. The disclosure provides a pharmaceutical composition wherein the highly purified extract of cannabis comprises at least about 95% CBD. The disclosure provides a pharmaceutical composition wherein the highly purified extract of cannabis comprises at least about 98% CBD. The disclosure provides a pharmaceutical composition wherein the highly purified extract of cannabis comprises at least about 99% CBD. The disclosure provides a pharmaceutical composition formulated as transdermal liquid formulation, transdermal semisolid formulation, or transdermal polymer matrix formulation. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, and combinations thereof. The disclosure provides a pharmaceutical composition further comprising carriers or ingredients in effective amount selected from the group consisting of solvents, gelling agents, polymers, penetration enhancers, emollients, skin irritation reducing agents, buffering agents, pH stabilizers, solubilizers, suspending agents, dispersing agents, stabilizers, plasticizers, surfactants, antioxidants, oxidants, and combinations thereof in the range of 0.01%-95% w/w or w/v. The disclosure provides a pharmaceutical composition wherein the carrier is present in the range of 0.01%-99.8% w/w or w/v. The disclosure provides a pharmaceutical composition which is formulated as a transdermal patch. The disclosure provides a pharmaceutical composition formulated as a transdermal patch, wherein the transdermal patch is selected from the group such as to reservoir patch, a microreservoir patch, a matrix patch, a pressure sensitive adhesive patch, extended release transdermal film a liquid reservoir system, a microreservoir patch, a matrix patch, a pressure sensitive adhesive patch, a mucoadhesive patch, and combinations thereof. The disclosure provides a pharmaceutical composition indicated for the treatment and/or prevention and/or control of seizure disorder in a patient, wherein the seizure disorder disorders include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, Tuberous Sclerosis Complex (TSC), Treatment-Resistant Epilepsy, Treatment Resistant Pediatric Epilepsy, mesial temporal lobe epilepsy, nocturnal frontal lobe epilepsy, progressive epilepsy with mental retardation, and progressive myoclonic epilepsy, as well as seizures associated with CNS mass lesions. The disclosure provides a pharmaceutical composition which is formulated as the transdermal formulation which can be administered in a dosage regimen selected from the group consisting of once daily, twice daily, three times a day, once in 1-8 hrs, once in 1-24 hrs, once in two days, once in three days, once in four days, once in five days, once in six days, once in a week, once in a 8 to about 13 days, once in two weeks, once in 15 days to about 30 days. The disclosure provides a pharmaceutical composition which may be formulated as microneedles. The disclosure provides a pharmaceutical composition wherein said CBD or derivative thereof is produced by a synthetic route. The disclosure provides a pharmaceutical composition co-administered with at least one additional an anti-epileptic agent selected from the group consisting of: clobazam; levetiracetam; topiramate; stiripentol; phenobarbital; lacsamide; valproic acid; zonisamide; perampanel; and fosphenytoin. The disclosure provides a pharmaceutical composition further comprising at least one additional an anti-epileptic agent selected from the group consisting of: clobazam; levetiracetam; topiramate; stiripentol; phenobarbital; lacsamide; valproic acid; zonisamide; perampanel; and fosphenytoin.

The disclosure provides a pharmaceutical composition comprising a highly purified extract of cannabis which comprises at least about 90% (w/w) cannabidiol (CBD), in a dosage form for transdermal delivery wherein the pharmaceutical composition comprises: about 9% to about 12% w/w of the highly purified CBD; optionally, about 30% to about 99% solvent; optionally, about 1% to about 20% penetration enhancer(s), wherein the pH of the composition is maintained at approximately 4.0 to 8.0. The disclosure provides a pharmaceutical composition formulated as transdermal liquid formulation, transdermal semisolid formulation, or transdermal polymer matrix formulation. The disclosure provides a pharmaceutical composition further comprising carriers or ingredients in effective amount selected from the group consisting of gelling agents, polymers, emollients, skin irritation reducing agents, buffering agents, pH stabilizers, solubilizers, suspending agents, dispersing agents, stabilizers, plasticizers, surfactants, antioxidants, oxidants, and combinations thereof. The disclosure provides a pharmaceutical composition further comprising carriers or ingredients in effective amount selected from the group consisting of gelling agents, polymers, emollients, skin irritation reducing agents, buffering agents, pH stabilizers, solubilizers, suspending agents, dispersing agents, stabilizers, plasticizers, surfactants, antioxidants, oxidants, and combinations thereof in the range of 0.01%-95% w/w or w/v. The disclosure provides a pharmaceutical composition which is formulated as a transdermal patch. The disclosure provides a pharmaceutical composition formulated as a transdermal patch, wherein the transdermal patch is selected from the group such as to reservoir patch, a microreservoir patch, a matrix patch, a pressure sensitive adhesive patch, extended release transdermal film a liquid reservoir system, a microreservoir patch, a matrix patch, a pressure sensitive adhesive patch, a mucoadhesive patch, and combinations thereof. The disclosure provides a pharmaceutical composition indicated for the treatment and/or prevention and/or control of seizure disorder in a patient, wherein the seizure disorder disorders include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, Tuberous Sclerosis Complex (TSC), Treatment-Resistant Epilepsy, Treatment Resistant Pediatric Epilepsy, mesial temporal lobe epilepsy, nocturnal frontal lobe epilepsy, progressive epilepsy with mental retardation, and progressive myoclonic epilepsy, as well as seizures associated with CNS mass lesions. The disclosure provides a pharmaceutical composition which is formulated as the transdermal formulation which can be administered in a dosage regimen selected from the group consisting of once daily, twice daily, three times a day, once in 1-8 hrs, once in 1-24 hrs, once in two days, once in three days, once in four days, once in five days, once in six days, once in a week, once in a 8 to about 13 days, once in two weeks, once in 15 days to about 30 days. The disclosure provides a pharmaceutical composition which may be formulated as microneedles. The disclosure provides a pharmaceutical composition wherein said CBD or derivative thereof is produced by a synthetic route. The disclosure provides a pharmaceutical composition co-administered with at least one additional an anti-epileptic agent selected from the group consisting of: clobazam; levetiracetam; topiramate; stiripentol; phenobarbital; lacsamide; valproic acid; zonisamide; perampanel; and fosphenytoin. The disclosure provides a pharmaceutical composition further comprising at least one additional an anti-epileptic agent selected from the group consisting of: clobazam; levetiracetam; topiramate; stiripentol; phenobarbital; lacsamide; valproic acid; zonisamide; perampanel; and fosphenytoin.

The disclosure provides a method for the treatment and/or prevention and/or control of seizure disorder in a patient comprising: selecting a patient in need of treatment and/or prevention and/or control of seizure disorder; topically applying the pharmaceutical composition as disclosed herein. The disclosure provides a method wherein the seizure disorder includes complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, Tuberous Sclerosis Complex (TSC), Treatment-Resistant Epilepsy, Treatment Resistant Pediatric Epilepsy, mesial temporal lobe epilepsy, nocturnal frontal lobe epilepsy, progressive epilepsy with mental retardation, and progressive myoclonic epilepsy, as well as seizures associated with CNS mass lesions. The disclosure provides a method wherein the topical application of a transdermal patch for the treatment and/or prevention and/or control of seizure disorder in a patient, wherein the seizure disorder include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, Tuberous Sclerosis Complex (TSC), Treatment-Resistant Epilepsy, Treatment Resistant Pediatric Epilepsy, mesial temporal lobe epilepsy, nocturnal frontal lobe epilepsy, progressive epilepsy with mental retardation, and progressive myoclonic epilepsy, as well as seizures associated with CNS mass lesions is selected from the group consisting of once in a day, once in two days, once in three days, once in four days, once in five days, once in six days, once in a week, once in ten days. The disclosure provides a method further providing a constant rate of delivery of the active components of the transdermal patch over a time period. The disclosure provides a method further providing a steady absorption rates of the active components of the transdermal patch over a time period. The disclosure provides a method further achieving a constant blood serum levels of the active components of the transdermal patch over a time period. The disclosure provides a method further achieving a reduced variability in dosage of the active components of the transdermal patches over a time period. The disclosure provides a method further providing a plasma concentration of the active components of the transdermal patch in a therapeutic range over a period of time.

The disclosure provides for the use of the compositions of the disclosure for the production of a medicament for treating the indications as set forth herein.

In accordance with a further embodiment, the present disclosure provides a use of the pharmaceutical compositions described above, an amount effective for use in a medicament, and most preferably for use as a medicament for treating a disease or disorder in a subject, for example as disclosed herein.

In accordance with yet another embodiment, the present disclosure provides a use of the pharmaceutical compositions described above, and at least one additional therapeutic agent, in an amount effective for use in a medicament, and most preferably for use as a medicament for treating a disease or disorder associated with disease in a subject, for example as disclosed herein.

DETAILED DESCRIPTION

Cannabinoids are a group of 21-carbon-containing terpenophenolic compounds produced by Cannabis species. Cannabinoids may also be synthetically produced. The term "cannabinoid" refers hereinafter to a class of diverse chemical compounds that act on cannabinoid receptors on cells that repress neurotransmitter release in the brain. These receptor proteins include the endocannabinoids (produced naturally in the body by humans and animals), the phytocannabinoids (found in cannabis and some other plants), and synthetic cannabinoids. Lipophilic cannabinoids are generally grouped as endocannabinoids (most typically as mammalian endocannabinoids); phytocannabinoids, from plant sources; and synthetic cannabinoids. Such cannabinoids are also often classified into the following subclasses: Cannabigerols (CBG); Cannabichromenes (CBC); Cannabidiol (CBD); Tetrahydrocannabinol (THC); Cannabinol (CBN); Cannabidiol (CBDL); Cannabicyclol (CBL); Cannabielsoin (CBE); and, Cannabitriol (CBT).

Cannabidiol IUPAC Name 2-[(1R,6R)-6-isopropenyl-3-methylcyclohex-2-en-1-yl]-5-pentylbenzene-1,3-diol Chemical Formula: $C_{21}H_{30}O_2$ Molecular weight: 314.46 dalton Chemical structure is shown below as formula I Formula I

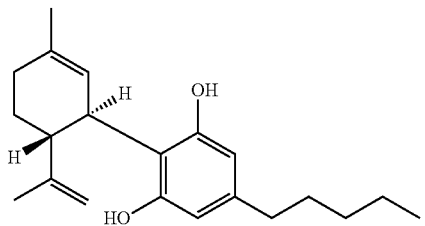

Tetrahydrocannbinol (THC) IUPAC Name (−)-(6aR, 10aR)-6,6,9-Trimethyl-3-pentyl-6a,7,8,10a-tetrahydro-6H-benzo[c]chromen-1-ol Chemical Formula: $C_{21}H_{30}O_2$ Molecular weight: 314.47 dalton.

Chemical structure is shown below as formula II

Formula II

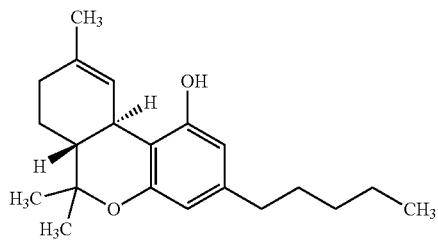

As used herein, the word cannabis refers to all pharmaceutically acceptable forms of cannabis and its derivatives either alone or in combinations thereof, for example, in following forms but not limited to such as free base or salts or isomers or amorphous or crystalline or co crystalline or solid solution or prodrugs or analogs or derivatives or metabolites. For example, cannabidiol's free base or its salts or its isomers or its amorphous form or its crystalline form or its co crystalline form or its solid solution or its prodrugs or its analogs or its derivatives or synthetic forms. The compound may be in the form of, for example, a pharmaceutically acceptable salt, such as an acid addition salt or a base salt, or a solvate thereof, including a hydrate thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts.

As used herein, the term "cannabidiol" includes the free base thereof, salts thereof, isomers thereof, amorphous forms thereof, crystalline forms thereof, co crystalline forms thereof, prodrugs thereof, analogs thereof, derivatives thereof, and synthetic forms thereof, alone or in combinations thereof. In certain embodiments the CBD is highly purified. In certain embodiments the CBD is present as a highly purified extract of cannabis which comprises at least 90%, 91%, 92%, 93%, 94%, 95%, 96%, 97%, 98%, 99%, 99.5%, or 99.75% (w/w) CBD. In exemplary embodiments, formulations of the disclosure may comprise CBD as disclosed herein at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 9.1%, about 9.2%, about 9.3%, about 9.4%, about 9.5%, about 9.6%, about 9.7%, about 9.8%, about 9.9% about 9.25%, about 9.5%, about 9.75%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise CBD at a concentration of about 1 to 25%, of about 5% to 20%, about 8% to about 15%, or about 9% to about 14%, about 9% to about 13%, about 9% to about 12%, w/w of the formulation. In certain embodiments, the dose of CBD is greater than, for example, about 1, 2, 3, 4, 5, 6, 7, 8, 9, 10, 15, 20, 25, 30, 35, 40, or 45 mg/kg/day. In certain embodiments, the dose of CBD is greater than, for example, about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, or 275 mg/day.

As used herein, the term "pharmaceutically acceptable salts" includes acid addition salts or addition salts of free bases. The term "pharmaceutically acceptable salts" of the cannabidiol within its scope all the possible isomers and their mixtures, and any pharmaceutically acceptable metabolite, biprecursor and/or pro-drug, such as, for example, a compound which has a structural formula different from the one of the compounds of the disclosure, and yet is directly or indirectly converted in vivo into a compound of the disclosure, upon administration to a subject, such as a mammal, particularly a human being.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is a human. As used herein, the term "agent" refers to any molecule, compound, methodology and/or substance for use in the prevention, treatment, management and/or diagnosis of a disease or condition. As used herein, the term "effective amount" refers to the amount of a therapy that is sufficient to result in the prevention of the development, recurrence, or onset of a disease or condition, and one or more symptoms thereof, to enhance or improve the prophylactic effect(s) of another therapy, reduce the severity, the duration of a disease or condition, ameliorate one or more symptoms of a disease or condition, prevent the advancement of a disease or condition, cause regression of a disease or condition, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "therapeutic agent" refers to any molecule, compound, and/or substance that is used for treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

The term "derivative" or "derivatized" as used herein includes, for example, chemical modification of a compound of the disclosure, or extracted from botanical sources or pharmaceutically acceptable salts thereof or mixtures thereof. That is, a "derivative" may be a functional equivalent of a compound of the disclosure, which is capable of inducing the improved pharmacological functional activity in a given subject.

As used herein, the terms "composition" and "formulation" are used interchangeably.

As used herein, the term "transdermal delivery" means delivery of drug into systemic circulation through the skin.

According to certain embodiments, transdermal compositions described herein are for the treatment and/or prevention and/or control of seizure disorder in a patient, wherein the seizure disorder disorders include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, mesial temporal lobe epilepsy, nocturnal frontal lobe epilepsy, progressive epilepsy with mental retardation, and progressive myoclonic epilepsy, as well as seizures associated with CNS mass lesions.

Epilepsy

Epilepsy is a brain disorder characterized by repeated seizures over time. Types of epilepsy can include, but are not limited to generalized epilepsy, e.g., childhood absence epilepsy, juvenile myoclonic epilepsy, epilepsy with grand-mal seizures on awakening, West syndrome, Lennox-Gastaut syndrome, Dravet syndrome, Tuberous Sclerosis Complex (TSC), Treatment-Resistant Epilepsy, Treatment Resistant Pediatric Epilepsy, partial epilepsy, e.g., temporal lobe epilepsy, frontal lobe epilepsy, benign focal epilepsy of childhood.

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

Purified CBD

The disclosure provides that the CBD is present in an amount that reduces total seizure frequency by greater than 70% with respect to the seizure frequency achieved on concomitant anti-epileptic drugs (AED). More preferably the CBD is present in an amount that reduces total seizure frequency by greater than 90% with respect to the seizure frequency achieved on concomitant anti-epileptic drugs (AED). More preferably still the CBD is present in an amount that reduces total seizure frequency by 100% with respect to the seizure frequency achieved on concomitant anti-epileptic drugs (AED).

In one embodiment the CBD is present as a highly purified extract of cannabis which comprises at least 90%, 91%, 92%, 93%, 94%, 95%, 96%, 97%, 98%, 99%, 99.5%, or 99.75% (w/w) CBD.

The one or more AED is preferably selected from the group consisting of: clobazam; levetiracetam; topiramate; stiripentol; phenobarbital; lacsamide; valproic acid; zonisamide; perampanel; and fosphenytoin. In certain embodiments the CBD is used in combination with clobazam. Preferably the number of different anti-epileptic drugs or the dose of AED that are used in combination with the CBD is reduced. More preferably the dose of AED which is reduced is of clobazam.

In certain embodiments, the dose of CBD is greater than, for example, about 1, 2, 3, 4, 5, 6, 7, 8, 9, 10, 15, 20, 25, 30, 35, 40, or 45 mg/kg/day. For example, a for a 15 kg patient a dose of greater than 75 mg of CBD per day would be provided. Doses greater than 5 mg/kg/day such as greater than 10/mg/kg/day, greater than 15 mg/kg/day, greater than 20 mg/kg/day and greater than 25 mg/kg/day are also envisaged to be effective. In certain embodiments, the dose of CBD is greater than, for example, about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, or 275 mg/day.

The disclosure provides a method of treating treatment-resistant epilepsy comprising administering cannabidiol (CBD) to a subject, wherein the epilepsy is febrile infection related epilepsy syndrome (FIRES).

The disclosure provides a method of treating treatment-resistant epilepsy comprising administering cannabidiol (CBD) to a subject in an amount sufficient to reduce total seizure frequency by greater than 50% with respect to the seizure frequency achieved on one or more concomitant anti-epileptic drugs (AED).

Pharmaceutical Compositions

According to certain embodiments described herein, pharmaceutical composition or transdermal formulation of contains highly purified CBD. More preferably transdermal formulation may include highly purified CBD.

One embodiment of the present disclosure can be a transdermal drug delivery system which may include without any limitation to transdermal formulation, transdermal patches, topical formulation, microneedles, iontophoresis, metered dose transdermal spray.

Transdermal formulation which includes liquids for example without any limitation like solutions, suspensions, dispersions, emulsion. Transdermal formulation includes semisolids for example without any limitations like gels, ointments, emulsions, creams, suspension, paste, lotion, balm. Liquid formulation and/or gel formulation incorporated in transdermal patch is preferred. Transdermal formulations which includes polymer matrix without any limitations like adhesive matrix, non-adhesive matrix.

Without any limitation, transdermal patch may include all transdermal drug delivery systems stated in art preferably but not limited to reservoir patch, matrix patch, bilayer matrix patch, multilayer matrix patch, microreservoir patch, adhesive systems, transdermally applicable tape and other.

In certain embodiments of the present disclosure, a transdermal patch comprises transdermal formulation containing highly purified CBD contained in a reservoir or a matrix, and an adhesive which allows the transdermal patch to adhere to the skin, allowing the passage of the highly purified CBD from the transdermal patch through the skin of the patient. The transdermal delivery system can be occlusive, semi-occlusive or non-occlusive, and can be adhesive or non-adhesive.

The transdermal formulation comprising highly purified CBD can be incorporated within the patch and patch can be applied topically to the skin surface. The patch can be left on the subject for any suitable period of time.

In some embodiments, the transdermal patches provide for a constant rate of delivery of the active components of the transdermal patch over a predetermined time period. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein provide a steady absorption rate of the active components of the transdermal patches by the patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein provide a constant blood serum level of the active components of the transdermal patches in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein provide a plasma concentration of the active components of the transdermal patches in a therapeutic range in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal patches described herein allow for reduced variability in dosage of active components in a patient over a predetermined time. In some embodiments, the predetermined time period is 24 hours, 48 hours, 72 hours, 96 hours, 120 hours, 144 hours, 7 days, 8 to 13 days, two weeks, or 15 days.

The topical formulation stated in the art which include, for example without any limitation, semisolids such as ointment, cream, emulsion, micro emulsion, nano emulsion, paste, balms, gels, lotions, mousses. Liquids such as solutions, suspensions, micro suspension, nano suspension, dispersions, nano dispersion etc. Sprays, aerosols, magma, etc. The topical formulation comprising highly purified CBD can be topically applied to the skin surface for transdermal delivery of cannabidiol.

The transdermal formulation and/or topical formulation of some embodiments of the present disclosure may include carriers or ingredients in effective amount either alone or in combinations thereof without any limitation to the following carriers or ingredients such as solvents, gelling agents, polymers, biodegradable polymers, penetration enhancers, emollients, skin irritation reducing agents, buffering agents, pH stabilizers, solubilizers, suspending agents, dispersing agents, stabilizers, plasticizers, tackifiers, surfactants, volatile chemicals, antioxidants, oxidants, chelating agents, complexing agents, diluents, excipients, material to prepare patch, material to prepare matrix patch, material to prepare reservoir patch etc.

Cannabidiol may be dissolved, suspended, dispersed or uniformly mixed in the above stated single carrier, mixture of carriers and combinations of carrier. Any combination of two or more drugs such as cannabidiol may be dissolved, suspended, dispersed or uniformly mixed in the above stated single carrier, mixture of carriers and combinations of carrier.

The desired optimum transdermal and/or topical formulation of cannabidiol alone or in combinations thereof may comprise without any limitation to following carriers as stated from example 1 to example 11 either alone or in combinations thereof.

The invention will be illustrated in more detail with reference to the following Examples, but it should be understood that the present invention is not deemed to be limited thereto.

EXAMPLES

Example 1

The transdermal formulation and/or topical formulation of the disclosure may comprise solvents known to those skilled in the art either alone or in combinations thereof without any limitation to following like alcohol $C_1$-$C_{20}$ such as but not limited to (methanol, ethanol, isopropyl alcohol, butanol, propanol etc.), polyhydric alcohols, glycols such as but not limited to (propylene glycol, polyethylene glycol, dipropylene glycol, hexylene glycol, butyene glycol, glycerine etc.), derivative of glycols, pyrrolidone such as but not limited to (N methyl 2-pyrrolidone, 2-pyrrolidone etc.), sulfoxides such as but not limited to (dimethyl sulfoxide, decymethylsulfoxide etc), dimethylisosorbide, mineral oils, vegetable oils, water, polar solvents, semi polar solvents, non polar solvents, volatile chemicals which can be used to make matrix patch such as but not limited to (ethanol, propanol, ethyl acetate, acetone, methanol, dichloromethane, chloroform, toluene, IPA), acids such as but not limited to acetic acid, lactic acid, levulinic acid, bases and others. More preferably in the range of 0.01%-95% w/w or w/v. In exemplary embodiments, formulations of the disclosure may comprise solvent(s) at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise solvent(s) at a concentration of about 30 to 99%, of about 35% to 95%, about 40% to about 90% w/w. In exemplary formulations of the disclosure, the solvent(s) will represent approximately 1 wt % to 75 wt %, preferably 2 wt % to 30 wt %, more preferably 5 wt. % to 20 wt. % of the formulation.

Example 2

The transdermal formulation and/or topical formulation of the disclosure may comprise gelling agents and/or thickening and/or suspending agents known to those skilled in the art either alone or in combinations thereof without any limitation to following like natural polymers, polysaccharides and its derivatives such as but not limited to (agar, alginic acid and derivatives, cassia tora, collagen, gelatin, gellum gum, guar gum, pectin, potassium, or sodium carageenan, tragacanth, xantham, gum copal, chitosan, resin etc.), semisynthetic polymers and its derivatives such as without any limitation to cellulose and its derivatives (methylcellulose, ethyl cellulose, carboxymethyl cellulose, hydroxylpropyl cellulose, hydroxylpropylmethyl cellulose etc.), synthetic polymers and its derivatives such as without any limitation to carboxyvinyl polymers or carbomers (carbopol 940, carbopol 934, carbopol 971p NF), polyethylene, and its copolymers etc, clays such as but not limited to (silicates, bentonite), silicon dioxide, polyvinyl alcohol, acrylic polymers (eudragit), acrylic acid esters, polyacrylate copolymers, polyacrylamide, polyvinyl pyrrolidone homopolymer and polyvinyl pyrrolidone copolymers such as but not limited to (PVP, Kollidon 30, poloxamer), isobutylene, ethyl vinyl acetate copolymers, natural rubber, synthetic rubber, pressure sensitive adhesives such as silicone polymers such as but not limited to (bio psa 4302, bio-psa 4202 etc.,), acrylic pressure sensitive adhesives such as but not limited to (duro-tak 87-2156, duro-tak 387-2287, etc.), polyisobutylene such as but not limited to (polyisobutylene low molecular weight, plyisobutylene medium molecular weight, polyisobutylene 35000 mw, etc), acrylic copolymers, rubber based adhesives, hot melt adhesives, styrene-butadiene copolymers, bentonite, all water and/or organic solvent swellable polymers, etc. More preferably in the range of 0.1% 70% w/w or w/v. In exemplary embodiments, formulations of the disclosure may comprise gelling agents and/or thickening and/or suspending agents at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise gelling agents and/or thickening and/or suspending agents at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the gelling agents and/or thickening and/or suspending agents will represent approximately 1 wt % to 75 wt %, preferably 2 wt % to 30 wt %, more preferably 5 wt. % to 20 wt. % of the formulation.

Example 3

The transdermal formulation and/or topical formulation of the disclosure may comprise penetration or permeation enhancers known to those skilled in the art either alone or in combination thereof without any limitation to the following, such as sulfoxides, and similar chemicals such as but not limited to (dimethylsulfoxide, dimethylacetamide, dimethylformamide, decymethylsulfoxide, dimethylisosorbide etc), 1,3-butanediol, azone, pyrrolidones such as but not limited to (N-methyl-2-pyrrolidone, 2-pyrrolidon etc.), esters, fatty acid esters such as but not limited to (propylene glycol monolaurate, butyl ethanoate, ethyl ethanoate, isopropyl myristate, isopropyl palmitate, methyl ethanoate, decyl oleate, glycerol monooleate, glycerol monolaurate, methyl laurate, lauryl laurate etc.), fatty acids such as but not limited to (capric acid, caprylic acid, lauric acid, oleic acid, myristic acid, linoleic acid, stearic acid, palmitic acid etc.), alcohols, fatty alcohols and glycols such as but not limited to (oleyl alcohol, nathanol, dodecanol, propylene glycol, glycerol etc.), ethers alcohol such as but not limited to (diethylene glycol monoethyl ether), urea, triglycerides such as but not limited to triacetin, polyoxyethylene fatty alcohol ethers, polyoxyethylene fatty acid esters, esters of fatty alcohols, essential oils, surfactant type enhancers such as but not limited to (brij, sodium lauryl sulfate, tween, polysorbate), terpene, terpenoids and all penetration or permeation enhancers referred in the book "Percutaneous Penetration Enhancers" (Eric W. Smith, Howard I. Maibach, 2005. November, CRC press). More preferably in the range of 0.01%-95% w/w or w/v. In exemplary embodiments, formulations of the disclosure may comprise permeation enhancer(s) at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise penetration or permeation enhancer(s) at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the permeation enhancer(s) will represent approximately 1 wt % to 75 wt %, preferably 2 wt % to 30 wt %, more preferably 5 wt. % to 20 wt. % of the formulation.

Example 4

The transdermal formulation and/or topical formulation of the disclosure may comprise plasticizers known to those skilled in the art either alone or in combination thereof without any limitation to following like glycerol and its esters, phosphate esters, glycol derivatives, sugar alcohols, sebacic acid esters, citric acid esters, tartaric acid esters, adipate, phthalic acid esters, triacetin, oleic acid esters and all the plasticizers which can be used in transdermal drug delivery system referred in the book "Handbook of Plasticizers" (George Wypych, 2004, Chem Tec Publishing). More preferably in the range of 0.01%-95% w/w or w/v. In exemplary embodiments, formulations of the disclosure may comprise plasticizer(s) at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise plasticizer(s) at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the plasticizer(s) will represent approximately 1 wt % to 75 wt %, preferably 2 wt % to 30 wt %, more preferably 5 wt. % to 20 wt. % of the formulation.

Example 5

The transdermal formulation and/or topical formulation of the disclosure may comprise emollients, humectants, skin irritation reducing agents and the similar compounds or chemicals known to those skilled in the art either alone or in combinations thereof without any limitation to following like petrolatum, lanolin, mineral oil, dimethicone, zinc oxide, glycerin, propylene glycol and others. More preferably in the range of 0.01%-95% w/w or w/v. In exemplary embodiments, formulations of the disclosure may comprise emollients, humectants, skin irritation reducing agents and the similar compounds or chemicals at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise emollients, humectants, skin irritation reducing agents and the similar compounds or chemicals at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the emollients, humectants, skin irritation reducing agents and the similar compounds or chemicals will represent approximately 1 wt % to 75 wt %, preferably 2 wt % to 30 wt %, more preferably 5 wt. % to 20 wt. % of the formulation.

Example 6

The transdermal formulation and/or topical formulation of the disclosure may comprise solubilizers, surfactants, emulsifying agents, dispersing agents and similar compounds or chemicals known to those skilled in the art either alone or in combination thereof without any limitation to following like polysorbate (e.g., TWEEN®) such as but not limited to (polysorbate 20, polysorbate 40, polysorbate 60, polysorbate 80, etc.), span such as but not limited to (span 80, span 20 etc.), surfactants such as (anionic, cationic, nonionic and amphoteric), propylene glycol monocaprylate type I, propylene glycol monocaprylate type II, propylene glycol dicaprylate, medium chain triglycerides, propylene glycol monolaurate type II, linoleoyl polyoxyl-6 glycerides, oleoyl-polyoxyl-6-glycerides, lauroyl polyoxyl-6-gylcerides, ethyl oleate, polyglyceryl-3-dioleate, diethylene glycol monoethyl ether, propylene glycol monolaurate type I, polyglyceryl-3-dioleate, caprylocaproyl polyoxyl-8 glycerides etc, cyclodextrins, LABRASOL® (a caprylocaproyl macrogolglyceride, Caprylocaproyl macrogol-8 glycerides EP, Caprylocaproyl polyoxyl-8 glycerides NF), and others. More preferably in the range of 0.01% 95% w/w or w/v. In exemplary embodiments, formulations of the disclosure may comprise solubilizers, surfactants, emulsifying agents, dispersing agents and similar compounds or chemicals at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise solubilizers, surfactants, emulsifying agents, dispersing agents and similar compounds or chemicals at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the solubilizers, surfactants, emulsifying agents, dispersing agents and similar compounds or chemicals will represent approximately 1 wt % to 75 wt %, preferably 2 wt % to 30 wt %, more preferably 5 wt. % to 20 wt. % of the formulation.

Example 7

Different techniques and ingredients can be used to increase the stability and/or solubility of highly purified CBD in formulation such as without any limitation to coating, encapsulation, microencapsulation, nanoencapsulation, lyophilization, chelating agents, complexing agents, etc.

Example 8

The transdermal formulation and/or topical formulation of the disclosure may comprise auxiliary pH buffering agents and pH stabilizers and similar compounds known to those skilled in the art which helps to maintain the appropriate pH of formulation preferably in the range of 4.0-8.0 either alone or in combination thereof without any limitation to following such as phosphate buffer, acetate buffer, citrate buffer, etc., acids such as but not limited to (carboxylic acids, inorganic acids, sulfonic acids, vinylogous carboxylic acids and others), base such as but not limited to (sodium hydroxide, potassium hydroxide, ammonium hydroxide, triethylamine, sodium carbonate, sodium bicarbonate) etc. More preferably in the range of 0.01%-30% w/w or w/v. In exemplary embodiments, formulations of the disclosure may comprise auxiliary pH buffering agents and pH stabilizers and similar compounds at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise auxiliary pH buffering agents and pH stabilizers and similar compounds at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the auxiliary pH buffering agents and pH stabilizers and similar compounds will represent approximately 1 wt % to 75 wt %, preferably 2 wt % to 30 wt %, more preferably 5 wt. % to 20 wt. % of the formulation. In certain embodiments, the pH of the formulation is maintained at about 4.0, about 4.5, about 5.0, about 5.5, about 6.0, about 6.5, about 7.0, about 7.5, or about 8.0. In certain embodiments, the pH of the formulation is maintained at a range of about 4.0 to about 8.0, about 4.5 to about 7.5, or about 5.0 to about 7.0.

Example 9

The transdermal formulation and/or topical formulation of the disclosure may comprise antioxidants such as but not limited to (sodium metabisulfite, citric acid, ascorbic acid, BHA, BHT), oxidizing agents, stabilizers, discoloring agents, preservatives and similar compounds or chemicals known to those skilled in the art which helps to get a stable formulation can be used either alone or in combination thereof without any limitation. More preferably in the range of 0.01%-50% w/w or w/v. In exemplary embodiments, formulations of the disclosure may comprise antioxidants at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, and about 80% of the formulation. In exemplary embodiments, formulations of the disclosure may comprise antioxidants at a concentration of about 1 to 20%, of about 5% to 25%, about 10% to about 20%, or about 15% to about 18%, about 30% to about 70%, about 35% to about 65%, and about 40% to about 64% w/w. In exemplary formulations of the disclosure, the antioxidants will represent approximately 1 wt % to 75 wt %, preferably 2 wt % to 30 wt %, more preferably 5 wt. % to 20 wt. % of the formulation.

Example 10

The transdermal formulation and/or topical formulation of the disclosure may be formulated in ointment and/or cream base known to those skilled in the art.

Example 11

Materials to make the transdermal delivery system of the disclosure in patch form known to those skilled in the art, for example, such as but not limited to reservoir patch, matrix patch, drug in adhesives, transdermal films and may include, such as but are not limited to polymers, copolymers, derivatives, backing film, release membranes, release liners, etc. either alone or in combinations thereof. Pressure sensitive adhesives (such as but not limited to silicone polymers, rubber based adhesives, acrylic polymers, acrylic copolymers, polyisobutylene, acrylic acid-isooctyl acrylate copolymer, hot melt adhesives, polybutylene etc.), backing film (such as but not limited to ethylene vinyl acetate copolymers, vinyl acetate resins, polyurethane, polyvinyl chloride, metal foils, polyester, aluminized films, polyethylene, etc.), release membrane (such as but not limited to microporous polyethylene membrane, microporous polypropylene membrane, rate controlling ethylene vinyl acetate copolymer membrane etc.), release liners (such as but not limited to siliconized polyester films, fluoropolymer coated polyester film, polyester film, siliconized polyethylene terephthalate film, etc.), tapes, etc.

The transdermal formulation and/or topical formulation and/or transdermal delivery system of the disclosure may deliver at least therapeutic effective dose of highly purified CBD. Therapeutic effective highly purified CBD, alone or in combinations thereof in human plasma required for treating and/or preventing pain and/or inflammation. Therapeutic effective highly purified CBD dose refers to the therapeutic concentration of in human plasma required for treating and/or preventing pain and/or inflammation. Furthermore, the precise therapeutic effective dose of highly purified CBD in the transdermal formulation or topical formulation or transdermal delivery system can be determined by those skilled in the art based on factors such as but not limited to the patient's condition etc. The transdermal formulation or topical formulation or transdermal delivery system will be available in different dosage strengths and patch sizes in order to achieve optimum therapeutic outcome based on patient's requirement.

In yet another embodiment, the transdermal formulation and/or topical formulation and/or transdermal delivery system of the disclosure may deliver at least therapeutic effective dose of highly purified CBD. Therapeutic effective highly purified CBD refers to the therapeutic concentration of highly purified CBD thereof in human plasma required for the treatment and/or prevention and/or control of seizure disorder in a patient, wherein the seizure disorder disorders include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, mesial temporal lobe epilepsy, nocturnal frontal lobe epilepsy, progressive epilepsy with mental retardation, and progressive myoclonic epilepsy, as well as seizures associated with CNS mass lesions.

The transdermal formulation or transdermal patch of highly purified CBD preferably but not limited to can be applied to the skin surface in any of the following dosage regimens such as once in a day, once in two days, once in three days, once in four days, once in five days, once in six days, once in a week, once in a 8 to about 13 days, once in two weeks, once in 15 days.

Example 12

Theoretical Flux Calculation for Cannabidiol

Oral bioavailability of CBD is only 13-19%. For our calculation purpose, TRPL took average bioavailability of 15%[2]. So, the actual dose delivering to patient upon oral delivery is described in Table 3

TABLE 3

Theoretical dose required from Transdermal Dosage form.

| Oral Dose | Dose range (mg/day) (based on Table 1) | Transdermal Dose range (mg/day) | Oral AUC (hr*ng/ml)[3] | Avg. Oral Plasma Concentration (ng/ml) |
|---|---|---|---|---|
| 5 mg/kg/day | 61-113 | 9-17 | 241 | 10.0 ng/ml |
| 10 mg/kg/day | 122-227 | 18-34 | 722 | 30.0 ng/ml |

$$\text{Flux Required} = \text{Dose}/\text{Surface area}$$

$$= 9 \text{ mg}/\text{day}/\text{surface area}$$

$$= 9000 \text{ ug}/24 \text{ hr}/50 \text{ sqcm}$$

$$= 7.5 \text{ ug}/\text{sqcm}/\text{hr}$$

So, 50 sqcm patch with 7.5 ug/sqcm/hr flux will deliver 9 mg of drug in one day. And 100 sqcm of patch will deliver 18 mg of drug with same flux profile. Some research articles showed oral bioavailability of CBD is in the range of 5-6%[2,8]

Example 13

Synthetic cannabidiol (CBD) formulations for transdermal delivery ((Formulation Nos. 001, 002, 003, 004, and 005) were prepared by mixing ingredients as shown in Table 4:

TABLE 4

Transdermal Synthetic Cannabidiol formulations

| Ingredients | 001 (% W/W) | 002 (% W/W) | 003 (% W/W) | 004 (% W/W) | 005 (% W/W) |
|---|---|---|---|---|---|
| CBD | 9.35 | 9.06 | 9.34 | 9.09 | 9.13 |
| PG | 90.65 | 45.51 | 45.17 | 45.54 | 45.33 |
| Hexylene Glycol | | 45.43 | | | |
| 1,3 Butanediol | | | 45.49 | | |
| PEG-400 | | | | 45.37 | |
| Dipropylene Glycol | | | | | 45.53 |

Abbreviations:
PG = propylene glycol;
CBD = Cannabidiol; PEG-400: Polyethylene Glycol-400.

All of the components from Table 2, with the exception of the CBD, were mixed together with stirring for 18 hours. Next, the CBD was added into the excipient mixture to prepare the final transdermal formulations.

The prepared transdermal formulations were then subjected to a flux measurement test as follows. Human cadaver skin, stored at −80° C., was thawed at room temperature in phosphate buffered saline (PBS), and visually inspected for defects before using in the study. Transdermal flux was then measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The donor compartment was filled with the transdermal CBD formulations prepared as described above. The receptor compartment was filled with receptor medium, held at constant temperature, and constantly stirred to collect the CBD as it diffuses through the skin and into receptor compartment. It is important to confirm that the receptor fluid is always in contact with the skin. The receptor compartment was emptied at 24 hr intervals for assay of CBD and replaced with fresh receptor solution. In order to maintain the sink condition in receptor compartment, it is important keep the CBD concentration in receptor compartment less than 10% of its solubility. The experimental conditions are provided in Table 3:

TABLE 5

Experimental Condition for In-vitro Permeability testing

| Receiving Media | De-ionized water + 0.5% Brij-O(20) + 0.01% Sodium Azide |
|---|---|
| Receiving Media Volume (mL) | 13 |
| Sample Volume (mL) | 13 |
| Sampling Interval (hr) | 24, 48, 72, 96, 120, 144 |
| Franz-cell diffusion area (sqcm) | 1.76 |
| Membrane Type | Human Cadaver Skin |

Flux of CBD through the human cadaver skin was measured for a minimum period of 96 Hrs (4 days) and results of the flux measurement are provided in Table 4.

TABLE 6

CBD Flux Results

| | 001 | 002 | 003 | 004 | 005 |
|---|---|---|---|---|---|
| Total Amount of CBD Permeated at 144 hrs (ng/cm$^2$) | 85795 | 167045 | 150000 | 59091 | 166477 |
| Flux (ng/cm$^2$/hr) | 338.5 | 1160.03 | 1041.66 | 410.35 | 1156.09 |

Example 14

Additional synthetic Cannabidiol (CBD) formulations for transdermal delivery (Formulation Nos. 006 through 014) were prepared by mixing ingredients as shown in Table 7:

TABLE 7

Transdermal Synthetic Cannabidiol formulation nos. 006 to 014

| Ingredients | 006 (% W/W) | 007 (% W/W) | 008 (% W/W) | 009 (% W/W) | 010 (% W/W) | 011 (% W/W) | 012 (% W/W) | 013 (% W/W) | 014 (% W/W) |
|---|---|---|---|---|---|---|---|---|---|
| CBD | 9.95 | 9.64 | 9.77 | 9.98 | 9.98 | 9.64 | 9.87 | 9.52 | 10.27 |
| PG | 42.70 | 42.58 | 42.51 | 42.51 | 42.02 | 42.45 | 42.47 | 42.34 | 42.09 |
| Hexylene Glycol | 42.36 | 42.48 | 42.40 | 42.63 | 42.66 | 42.77 | 42.50 | 42.64 | 42.39 |
| Tween-20 | 4.99 | | | | | | | | |
| Triacetin | | 5.30 | | | | | | | |
| PGML | | | 5.32 | | | | | | |
| OA | | | | 4.88 | | | | | |
| ML | | | | | 5.34 | | | | |
| EO | | | | | | 5.18 | | | |

TABLE 7-continued

Transdermal Synthetic Cannabidiol formulation nos. 006 to 014

| Ingredients | 006 (% W/W) | 007 (% W/W) | 008 (% W/W) | 009 (% W/W) | 010 (% W/W) | 011 (% W/W) | 012 (% W/W) | 013 (% W/W) | 014 (% W/W) |
|---|---|---|---|---|---|---|---|---|---|
| IPM | | | | | | | 5.16 | | |
| IPP | | | | | | | | 5.51 | |
| Labrasol | | | | | | | | | 5.25 |

Abbreviations:
CBD = Cannabidiol;
PGML: Propylene glycol monolaurate;
PG = propylene glycol;
OA = Oleyl Alcohol;
ML = Methyl Laurate;
EO = Ethyl Oleate;
IPM = Isopropyl Myristate;
IPP: Isopropyl Palmitate.

Synthetic Cannabidiol formulations for transdermal delivery (006-014) were prepared by the same procedure described in Example 2. Flux measurement was also performed as described in Example 2. The experimental conditions are the same as provided in Table 5 of Example 2.

Flux of CBD through the human cadaver skin was measured for a minimum period of 48 Hrs and results of the flux measurement experiments are provided in Table 8.

TABLE 8

CBD Flux Results

| | Formulation No. | | | | | | | | |
|---|---|---|---|---|---|---|---|---|---|
| | 006 | 007 | 008 | 009 | 010 | 011 | 012 | 013 | 014 |
| Total Amount of CBD Permeated at 48 hrs (ng/cm$^2$) | 27272 | 34091 | 39205 | 44318 | 34659 | 40341 | 38068 | 66477 | 28977 |
| Flux (ng/cm$^2$/hr) | 568.16 | 710.23 | 816.77 | 923.29 | 722.06 | 840.43 | 793.08 | 1384.94 | 603.69 |

Example 15

Additional synthetic cannabidiol (CBD) formulations for transdermal delivery patches (Formulation Nos. 015 to 018) were prepared by mixing ingredients as shown in Table 9:

TABLE 9

Transdermal Synthetic cannabidiol formulation nos. 015 to 018

| Ingredients | 015 (% W/W) | 016 (% W/W) | 017 (% W/W) | 018 (% W/W) |
|---|---|---|---|---|
| CBD | 2.0 | 2.0 | 2.0 | 2.0 |
| PG | 27.8 | 27.8 | 27.8 | 27.8 |
| Hexylene Glycol | 27.8 | 27.8 | 27.8 | 27.8 |
| Durotak 9301 | 42.4 | | | |
| Durotak 2516 | | 42.4 | | |
| Durotak 2207 | | | 42.4 | |
| Silicone Adhesive | | | | 42.4 |

To prepare a transdermal patch containing synthetic cannabidiol, all of the components from Table 9, with the exception of the CBD, were mixed together with stirring for 18 hours. Next, the CBD was added 30 minutes before spreading the formulation. The formulation was spread using a commercial benchtop spreader. Specifically, the formulation matrix is evenly spread onto an 8×14 inch sheet of release liner (such as 3M 9744) to a thickness of 0.5 mm. The sheet is then place in an oven at 100° F. for one hour to evaporate off the ethyl acetate and ethanol adhesive solvent. An opaque backing membrane (such as 3M 9730 NR film) with low permeability to oxygen, for inhibition of photo and oxidative degradation, is then carefully applied to the sheet by hand to avoid formation of bubbles and voids. A circular die (1.5 inches diameter) was used to cut patches (7 cm$^2$) for subsequent studies.

The general procedure for flux measurements of transdermal formulations in the examples above was as follows.

The human cadaver skin, stored at −80° C., was thawed at room temperature in PBS, and visually inspected for defects before use. Transdermal flux was measured using standard Franz diffusion cells composed of a cylindrical donor compartment and a separate water jacketed cylindrical receptor compartment with the volume of 13 mL. The human cadaver skin was clamped between the two compartments with the dermis side facing toward the receptor compartment. The general procedure for flux measurement of the transdermal adhesive patch is as follows. The release liner is peeled off the patch and the adhesive surface is applied to a piece of human cadaver skin (Example 15, Table 9 only). The transdermal patch was adhered to the skin with the patch on the side of the skin in contact with the donor compartment. The receptor compartment was filled with receptor medium, held at constant temperature, and constantly stirred to collect the CBD as it diffuses from the adhered patch, through the skin and into receptor compartment. It was confirmed that the receptor fluid was always in contact with the skin. The receptor compartment was emptied at 24 hour intervals for assay of CBD and replaced with fresh receptor solution. In order to maintain the sink condition in receptor compartment, the CBD concentration in the receptor compartment was maintained at less than 10% of its solubility. The experimental conditions are the same as provided in Table 5 of Example 13.

REFERENCES 1. www.accessdata.fda.gov/drugsatfda docs/label/2018/210365lbl.pdf
2. doi.org/10.1002/cpdd.408
3. Devinsky et. al., "Randomized dose-ranging safety trial of cannabidiol in Dravet Syndrome", Neurology, 90(14), 2018
4. www.ncbi.nlm.nih.gov/pmc/articles/PMC3763649/

While the disclosure has been described in detail and with reference to specific examples thereof, it will be apparent to one skilled in the art that various changes and modifications can be made therein without departing from the spirit and scope thereof.

What is claimed is:

1. A pharmaceutical composition comprising a highly purified cannabis which comprises at least about 90% (w/w) cannabidiol (CBD), in a dosage form for transdermal delivery wherein the pharmaceutical composition comprises:
   a concentration of the highly purified CBD selected from the group consisting of about 1%, about 2%, about 3%, about 4%, about 5%, about 6%, about 7%, about 8%, about 9%, about 10%, about 11%, about 12%, about 13%, about 14%, and about 15% w/w;
   about 5% to about 25% w/w of a solvent comprising propylene glycol;
   about 1% to about 20% w/w of a penetration enhancer comprising oleic acid;
   about 0.1 to 0.7% of butylated hydroxytoluene;
   about 2% to about 15% w/w of at least one suspending agent comprising silicon dioxide; and
   about 50% to about 80% w/w of a silicone pressure sensitive adhesive,
   wherein the pH of the composition is maintained at approximately 4.0 to 8.0,
   wherein the pharmaceutical composition is in the form of a transdermal matrix patch, further wherein the pharmaceutical composition provides a constant rate of delivery of the active components of the matrix patch in a therapeutic range in a patient over at least 7 days.

2. The pharmaceutical composition of claim 1 further comprising carriers or ingredients selected from the group consisting of polymers, emollients, skin irritation reducing agents, buffering agents, pH stabilizers, solubilizers, dispersing agents, stabilizers, plasticizers, surfactants, antioxidants, oxidants, and combinations thereof.

3. The pharmaceutical composition of claim 1 further comprising carriers or ingredients selected from the group consisting of polymers, emollients, skin irritation reducing agents, buffering agents, pH stabilizers, solubilizers, dispersing agents, stabilizers, plasticizers, surfactants, antioxidants, oxidants, and combinations thereof in the range of 0.01%-95% w/w or w/v.

4. The pharmaceutical composition of claim 1 indicated for the treatment of seizure disorder in a patient, wherein the seizure disorder is selected from the group consisting of complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, juvenile myoclonic epilepsy, Lennox-Gastaut, Dravet syndrome, Tuberous Sclerosis Complex (TSC), Treatment-Resistant Epilepsy, Treatment Resistant Pediatric Epilepsy, mesial temporal lobe epilepsy, nocturnal frontal lobe epilepsy, progressive epilepsy with mental retardation, and progressive myoclonic epilepsy, and seizures associated with CNS mass lesions.

5. The pharmaceutical composition of claim 1 which is formulated as the transdermal formulation which can be administered in a dosage regimen selected from the group consisting of once in a week, once in a 8 to about 13 days, once in two weeks, once in 15 days to about 30 days.

6. The pharmaceutical composition of claim 1 wherein said CBD is produced by a synthetic route.

7. The pharmaceutical composition of claim 1 co-administered with at least one additional anti-epileptic agent selected from the group consisting of: clobazam; levetiracetam; topiramate; stiripentol; phenobarbital; lacsamide; valproic acid; zonisamide; perampanel; and fosphenytoin.

8. The pharmaceutical composition of claim 1 further comprising at least one additional anti-epileptic agent selected from the group consisting of: clobazam; levetiracetam; topiramate; stiripentol; phenobarbital; lacsamide; valproic acid; zonisamide; perampanel; and fosphenytoin.

9. A method for the treatment of seizure disorder in a patient comprising: selecting a patient in need of treatment of seizure disorder; topically applying the pharmaceutical composition of claim 1.

10. The method of claim 9, wherein the seizure disorder includes complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, Tuberous Sclerosis Complex (TSC), Treatment-Resistant Epilepsy, Treatment Resistant Pediatric Epilepsy, mesial temporal lobe epilepsy, nocturnal frontal lobe epilepsy, progressive epilepsy with mental retardation, and progressive myoclonic epilepsy, as well as seizures associated with CNS mass lesions.

11. The method of claim 9 wherein the topical application of a transdermal patch for the treatment of seizure disorder in a patient, wherein the seizure disorder include, for example, complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, Dravet syndrome, Tuberous Sclerosis Complex (TSC), Treatment-Resistant Epilepsy, Treatment Resistant Pediatric Epilepsy, mesial temporal lobe epilepsy, nocturnal frontal lobe epilepsy, progressive epilepsy with mental retardation, and progressive myoclonic epilepsy, as well as seizures associated with CNS mass lesions is selected from the group consisting of once in a day, once in two days, once in three days, once in four days, once in five days, once in six days, once in a week, once in ten days.

12. The method of claim 9 further providing a constant rate of delivery of the active components of the transdermal patch over a time period.

13. The method of claim 9 further providing a steady absorption rates of the active components of the transdermal patch over a time period.

14. The method of claim 9 further achieving a constant blood serum levels of the active components of the transdermal patch over a time period.

15. The method of claim 9 further achieving a reduced variability in dosage of the active components of the transdermal patches over a time period.

16. The method of claim 9 further providing a plasma concentration of the active components of the transdermal patch in a therapeutic range over a period of time.

* * * * *